US008801432B2

(12) United States Patent
Kurti, Jr. et al.

(10) Patent No.: US 8,801,432 B2
(45) Date of Patent: Aug. 12, 2014

(54) DEVICE, SYSTEM AND METHODS FOR DETERMINING AND MEASURING TEMPOROMANDIBULAR JOINT POSITIONS AND MOVEMENTS

(71) Applicant: Loma Linda University, Loma Linda, CA (US)

(72) Inventors: Ralph S. Kurti, Jr., Phelan, CA (US); Keith E. Schubert, China Spring, TX (US); Serkan Inceoglu, Moreno Valley, CA (US); Mathew T. Kattadiyil, Redlands, CA (US)

(73) Assignee: Loma Linda Univeristy, Loma Linda, CA (US)

( * ) Notice: Subject to any disclaimer, the term of this patent is extended or adjusted under 35 U.S.C. 154(b) by 0 days.

(21) Appl. No.: 14/237,555

(22) PCT Filed: Jun. 26, 2013

(86) PCT No.: PCT/US2013/047991
§ 371 (c)(1),
(2), (4) Date: Feb. 6, 2014

(87) PCT Pub. No.: WO2014/004730
PCT Pub. Date: Jan. 3, 2014

(65) Prior Publication Data

US 2014/0186793 A1 Jul. 3, 2014

Related U.S. Application Data

(60) Provisional application No. 61/664,292, filed on Jun. 26, 2012.

(51) Int. Cl.
*A61C 19/04* (2006.01)
*A61C 9/00* (2006.01)
*A61B 19/00* (2006.01)
*A61B 5/00* (2006.01)
*A61C 19/045* (2006.01)

(52) U.S. Cl.
CPC ............... *A61B 5/4542* (2013.01); *A61B 19/54* (2013.01); *A61B 5/0088* (2013.01); *A61B 5/4836* (2013.01); *A61B 5/7282* (2013.01); *A61B 5/0075* (2013.01); *A61B 5/742* (2013.01); *A61C 19/045* (2013.01)
USPC ............................................... 433/73; 433/37

(58) Field of Classification Search
USPC ..................... 433/73, 56, 69, 75, 213, 37–38; 600/590
See application file for complete search history.

(56) References Cited

U.S. PATENT DOCUMENTS 1,052,806 A * 2/1913 Evans ............................ 433/73
3,056,205 A * 10/1962 Ennor ............................ 433/35

(Continued)

FOREIGN PATENT DOCUMENTS

WO W02014/004730 A2 1/2014

OTHER PUBLICATIONS

Loma Linda University, International Search Report and Written Opinion issued in parent International Patent Application No. PCT/US2013/047991 on Dec. 30, 2013.

(Continued)

*Primary Examiner* — Yogesh Patel
(74) *Attorney, Agent, or Firm* — David A. Farah; Sheldon Mak & Anderson PC

(57) ABSTRACT

A device for determining or measuring temporomandibular joint positions and movements of a patient. A method for determining or measuring one or more than one temporomandibular joint position or movement of a patient. A method of diagnosing a condition or disease of a temporomandibular joint of a patient.

49 Claims, 26 Drawing Sheets

50
50
70
72
10
10
10
10
74

(56) References Cited

U.S. PATENT DOCUMENTS

| | | | | |
|---|---|---|---|---|
| 3,577,855 | A * | 5/1971 | Baum | 33/514 |
| 4,681,539 | A | 7/1987 | Knap | |
| 4,687,003 | A | 8/1987 | Burckhardt | |
| 4,789,334 | A * | 12/1988 | Wedenig et al. | 433/37 |
| 5,078,600 | A | 1/1992 | Austin | |
| 5,143,086 | A | 9/1992 | Duret et al. | |
| 6,117,092 | A * | 9/2000 | Weinstein et al. | 600/590 |
| 6,302,690 | B1 * | 10/2001 | Brandhorst et al. | 433/45 |
| 2005/0075585 | A1 | 4/2005 | Kim et al. | |
| 2005/0251066 | A1 | 11/2005 | Mack | |
| 2007/0264609 | A1 | 11/2007 | Brunner et al. | |
| 2010/0075274 | A1 * | 3/2010 | Klett | 433/56 |
| 2010/0151409 | A1 | 6/2010 | Munehiro | |
| 2011/0027745 | A1 | 2/2011 | Evenson | |
| 2011/0124991 | A1 * | 5/2011 | Hoarau | 600/324 |
| 2011/0217674 | A1 | 9/2011 | Hanewinkel et al. | |

OTHER PUBLICATIONS

Loma Linda University, Response to Written Opinion and Article 34 Amendment and Chapter II Demand filed in parent International Patent Application No. PCT/US2013/047991 on Jan. 15, 2014.

* cited by examiner

DEVICE, SYSTEM AND METHODS FOR DETERMINING AND MEASURING TEMPOROMANDIBULAR JOINT POSITIONS AND MOVEMENTS

CROSS-REFERENCE TO RELATED APPLICATIONS

The present Application is a national phase of International Patent Application No. PCT/US2013/047991, titled "Device, System and Methods for Determining and Measuring Temporomandibular Joint Positions and Movements," filed Jun. 26, 2013, which claims the benefit of U.S. Provisional Patent Application No. 61/664,292, titled "Method and System for Determining And Measuring Temporomandibular Joint Positions and Movements," filed Jun. 26, 2012, the contents of which are incorporated in this disclosure by reference in their entirety.

BACKGROUND

The temporomandibular joint (TMJ) is a synovial joint formed by the junction of the temporal bone portion of the cranium (upper section of the joint) and the superior aspect of the mandible (lower section of the joint). Between the two bones of the temporomandibular joint is an articular disc dividing the temporomandibular joint into two compartments. The upper joint compartment (formed by the articular disk and the temporal bone) is involved in translational movement (movement in a sagittal plane). The lower joint compartment (formed by the mandible and the articular disc) is involved in rotational movement (movement around a transverse oriented axis). The complex movements of the temporomandibular joint render it susceptible to various conditions and diseases affecting the function of the temporomandibular joint, referred to generally as temporomandibular joint disorders or temporomandibular joint dysfunction (TMD). Among these conditions and diseases are ankylosis, arthritis, dislocations, genetic anomalies, neoplasia and trauma.

During the evaluation of temporomandibular joint function, prosthodontists and other dental specialists use clinical experience and published research to estimate the values for a variety of temporomandibular joint positions and movements, such as:

1) anterior guidance (touching of the teeth during eccentric movements of the mandible);
2) condylar guidance (the angle at which the condyle moves away from a horizontal reference plane from centric relation along the articular eminence of the mandibular fossa);
3) immediate side shift (the lateral movement of the condyles at the commencement of mandibular laterotrusion);
4) mediotrusion/laterotrusion (thrusting of the mandibular condyle inward toward the median plane/outward away from the median plane);
5) progressive side shift (also called the Bennet angle) (the angle obtained after the non-working side condyle has moved anteriorly and medially, relative to the sagittal plane);
6) retrusion/protrusion (position posterior to the normal position/anterior to the normal position); and
7) surtrusion/detrusion (upward thrust/downward thrust).

The values for these temporomandibular joint positions and movements are used to set a dental articulator to simulate motion for prosthetic design of dentures and crowns, and for masticatory assessment and masticatory research. Ideally, the values for temporomandibular joint positions and movements would be directly determined for every patient; however, disadvantageously, determining the values for temporomandibular joint positions and movements on a patient is time-consuming and expensive, and therefore is not usually done on each patient.

Therefore, there is a need for a new method for the measuring temporomandibular joint positions and movements that is not associated with the disadvantages of currently known methods.

SUMMARY

According to one embodiment of the present invention, there is provided a mandibular/maxillary reference device for determining or measuring temporomandibular joint positions and movements of a patient, where the patient has a maxilla with an inferior anterior portion and a mandible with a superior anterior portion. The device comprises a) a mouthpiece configured to fit the inferior anterior portion of the maxilla of the patient or the superior anterior portion of the mandible of the patient, the mouthpiece comprising an anterior end and a posterior end, and a plane 'p' passing from the anterior end of the mouthpiece to the posterior end of the mouthpiece; b) one or more than one support comprising a first posterior end, a second posterior end, an axial length 'l' from the first posterior end to the second posterior end, and one or more than one attachment position, where the one or more than one attachment element attaches the support to the mouthpiece at the one or more than one attachment position along the length 'l'; c) one or more than one attachment element attaching the one or more than one support to the mouthpiece; and d) one or more than one marker attached to the one or more than one support. In one embodiment, the mouthpiece is symmetric about the plane 'p.' In one embodiment, the mouthpiece is configured to interchangeably and reversibly fit both the inferior anterior portion of the maxilla of the patient and the superior anterior portion of the mandible of the patient by rotating the mandibular/maxillary reference device around an axis passing from the anterior end of the mouthpiece to the posterior end of the mouthpiece in plane 'p.' In one embodiment, the mouthpiece is a dental tray. In one embodiment, the mouthpiece is an occlusal plane indexing plate. In one embodiment, the mouthpiece is a buccal indexing fork. In one embodiment, the mouthpiece is a curved bracket configured to engage only facial and buccal surfaces of maxillary teeth or mandibular teeth of the patient thereby permitting the patient full occlusion when the mandibular/maxillary reference device is applied to the patient. In one embodiment, the curved bracket comprises a longitudinal cross-section and the longitudinal cross-section is oval or round. In one embodiment, the curved bracket comprises a longitudinal cross-section with a central surface and the central surface is concave or flat. In one embodiment, the mouthpiece is integrally attached to the attachment element. In one embodiment, the mouthpiece is reversibly attached to the attachment element. In one embodiment, the support is a curved bracket. In one embodiment, the curved bracket comprises a longitudinal cross-section and the longitudinal cross-section is oval or round. In one embodiment, the curved bracket comprises a longitudinal cross-section with an inner surface and the inner surface is concave or flat. In one embodiment, the one or more than one attachment position is one attachment position coinciding with the plane 'p.' In one embodiment, the one or more than one attachment position is two attachment positions. In one embodiment, the one or more than one attachment position is three attachment positions. In one embodiment, the one or more than one attachment position is four attachment positions. In one embodiment, the one or more than one attachment element is a flat plate. In one embodiment, one of the one or more than one attachment element is a tubular strut. In one embodiment, the one or more than one attachment element is one attachment element. In one embodiment, the one or more than one attachment element is two attachment elements. In one embodiment, the one or more than one attachment element is three attachment elements. In one embodiment, the one or more than one attachment element is four attachment elements. In one embodiment, the attachment element is integrally attached to the support. In one embodiment, the attachment element is reversibly attached to the support. In one embodiment, the one or more than one marker is two markers. In one embodiment, the one or more than one marker is three markers. In one embodiment, the one or more than one marker is four markers. In one embodiment, the one or more than one marker is more than four markers. In one embodiment, one marker is attached to the support coincident with the plane 'p.' In one embodiment, none of the one or more than one marker is attached to the support coincident with the plane 'p.' In one embodiment, the device comprises a plurality of markers, and two of the plurality of markers are positioned equidistantly from plane 'p' along the axial length 'l' of the support. In one embodiment, the device comprises a plurality of markers, and two of the plurality of markers are positioned non-equidistantly from plane 'p' along the axial length 'l' of the support. In one embodiment, the device comprises a plurality of markers, and two of the plurality of markers are positioned equidistantly from plane 'p' along the axial length 'l' of the support, and another marker is attached to the support coincident with the plane 'p.' In one embodiment, all of the one or more than one markers are integrally and non-movably attached to the support. In one embodiment, one or more of the one or more than one marker is movably attached to the support. In one embodiment, all of the one or more than one markers are movably attached to the support. In one embodiment, one or more of the one or more than one marker is removably attached to the support. In one embodiment, all of the one or more than one markers are removably attached from the support. In one embodiment, one or more of the one or more than one marker is an emitter of electromagnetic radiation. In one embodiment, all of the one or more than one markers are emitters of electromagnetic radiation. In one embodiment, one or more of the one or more than one marker is a reflector of electromagnetic radiation. In one embodiment, all of the one or more than one markers are reflectors of electromagnetic radiation. In one embodiment, one or more of the one or more than one marker is an emitter of electromagnetic radiation, and one or more of the one or more than one marker is a reflector of electromagnetic radiation. In one embodiment, one or more of the one or more than one marker emits or reflects electromagnetic radiation in the infrared wavelengths. In one embodiment, one or more of the one or more than one marker emits or reflects electromagnetic radiation in the ultraviolet wavelengths. In one embodiment, one or more of the one or more than one marker emits or reflects electromagnetic radiation in the visible wavelengths. In one embodiment, one or more of the one or more than one marker emits or reflects electromagnetic radiation in a first wavelength, range of wavelengths, group of wavelengths or group of ranges of wavelengths, and another of the one or more than one marker emits or reflects electromagnetic radiation in a second wavelength, range of wavelengths, group of wavelengths or group of ranges of wavelengths, where the first wavelength, range of wavelengths, group of wavelengths or group of ranges of wavelengths is different from the second wavelength, range of wavelengths, group of wavelengths or group of ranges of wavelengths.

According to another embodiment of the present invention, there is provided a mandibular/maxillary reference device for determining or measuring temporomandibular joint positions and movements of a patient, where the patient has a maxilla with an inferior anterior portion and a mandible with a superior anterior portion. The device comprises a) a buccal indexing fork mouthpiece, the mouthpiece comprising an anterior end and a posterior end, and a plane 'p' passing from the anterior end of the mouthpiece to the posterior end of the mouthpiece, where the mouthpiece is symmetric about the plane 'p'; b) one or more than one curved bracket support comprising a first posterior end, a second posterior end, an axial length 'l' from the first posterior end to the second posterior end, and one or more than one attachment position, where the one or more than one attachment element attaches the support to the mouthpiece at the one or more than one attachment position along the length 'l'; c) one or more than one attachment element attaching the one or more than one support to the mouthpiece; and d) one or more than one marker attached to the one or more than one support. In one embodiment, the device comprises a plurality of markers, and two of the plurality of markers are positioned equidistantly from plane 'p' along the axial length 'l' of the support, and another marker is attached to the support coincident with the plane 'p.' In one embodiment, none of the one or more than one marker is attached to the support coincident with the plane 'p'; and where three of the plurality of markers are positioned non-equidistantly from plane 'p' along the axial length 'l' of the support.

According to another embodiment of the present invention, there is provided a mandibular/maxillary reference device for determining or measuring temporomandibular joint positions and movements of a patient, where the patient has a maxilla with an inferior anterior portion and a mandible with a superior anterior portion. The device comprises a) an occlusal plane indexing plate mouthpiece comprising an anterior end and a posterior end, and a plane 'p' passing from the anterior end of the mouthpiece to the posterior end of the mouthpiece, where the mouthpiece is symmetric about the plane 'p'; b) one or more than one curved bracket support comprising a first posterior end, a second posterior end, an axial length 'l' from the first posterior end to the second posterior end, and one or more than one attachment position, where the one or more than one attachment element attaches the support to the mouthpiece at the one or more than one attachment position along the length 'l'; c) one or more than one attachment element attaching the one or more than one support to the mouthpiece; and d) one or more than one marker attached to the one or more than one support. In one embodiment, the device comprises a plurality of markers, and two of the plurality of markers are positioned equidistantly from plane 'p' along the axial length 'l' of the support, and another marker is attached to the support coincident with the plane 'p.' In one embodiment, none of the one or more than one markers are attached to the support coincident with the plane 'p'; and where three of the plurality of markers are positioned non-equidistantly from plane 'p' along the axial length 'l' of the support.

According to another embodiment of the present invention, there is provided an upper face reference device for determining or measuring temporomandibular joint positions and movements of a patient, where the patient has a cranium with eyes, a nose with a bridge, an auricle with a superior aspect. The device comprises a) a frontal section configured to fit over the eyes and the bridge of the nose of the patient, the frontal section comprising two lateral ends and a length 'l' between the two lateral ends, and a plane 'p' passing equidistantly between one lateral end of the frontal section and the other lateral end of the frontal section; b) two lateral sections, each lateral section configured to fit between the superior aspect of the auricle and the cranium of the patient, where each lateral section comprises an anterior end and a posterior end, where the anterior end of each lateral section is attached to one of the two lateral ends of the frontal section; and c) one or more than one marker attached to the frontal section, or to one or both of the lateral sections, or to both the frontal section and to one or both of the lateral sections. In one embodiment, the anterior end of each lateral section is attached to one of the two lateral ends of the frontal section by a hinge mechanism allowing movement of the posterior end of one lateral section closer to and farther from the posterior end of the other lateral section. In one embodiment, the one or more than one marker is two markers. In one embodiment, the one or more than one marker is three markers. In one embodiment, the one or more than one marker is four markers. In one embodiment, the one or more than one marker of the upper face reference device is more than four markers. In one embodiment, the device is symmetric about the plane 'p.' In one embodiment, the device is asymmetric about the plane 'p.' In one embodiment, one of the one or more than one marker is attached to the frontal section coincident with the plane 'p.' In one embodiment, one of the one or more than one marker is attached to the frontal section non-coincident with the plane 'p.' In one embodiment, one of the one or more than one marker is attached to one lateral section a first distance from the anterior end of the lateral section, and another of the one or more than one marker is attached to the other lateral section a second distance from the anterior end of the other lateral section, and the first distance is equal to the second distance. In one embodiment, one of the one or more than one marker is attached to one lateral section a first distance from the anterior end of the lateral section, and another of the one or more than one marker is attached to the other lateral section a second distance from the anterior end of the other lateral section, and the first distance is unequal to the second distance. In one embodiment, one marker is attached to the frontal section coincident with the plane 'p,' another marker is attached to one lateral section a first distance from the anterior end of the lateral section, and another marker is attached to the other lateral section a second distance from the anterior end of the other lateral section, where the first distance is equal to the second distance. In one embodiment, one marker is attached to the frontal section non-coincident with the plane 'p,' another marker is attached to one lateral section a first distance from the anterior end of the lateral section, and another marker is attached to the other lateral section a second distance from the anterior end of the other lateral section, where the first distance is equal to the second distance. In one embodiment, one marker is attached to the frontal section non-coincident with the plane 'p,' another marker is attached to one lateral section a first distance from the anterior end of the lateral section, and another marker is attached to the other lateral section a second distance from the anterior end of the other lateral section, where the first distance is unequal to the second distance. In one embodiment, all of the one or more than one markers are integrally and non-movably attached to the device. In one embodiment, one or more of the one or more than one marker is movably attached to the device. In one embodiment, all of the one or more than one markers are movably attached to the device. In one embodiment, one or more of the one or more than one marker is removably attached to the device. In one embodiment, all of the one or more than one markers are removably attached to the device. In one embodiment, one or more of the one or more than one marker is an emitter of electromagnetic radiation. In one embodiment, all of the one or more than one markers are emitters of electromagnetic radiation. In one embodiment, one or more of the one or more than one marker is a reflector of electromagnetic radiation. In one embodiment, all of the one or more than one markers are reflectors of electromagnetic radiation. In one embodiment, one or more of the one or more than one marker is an emitter of electromagnetic radiation, and one or more of the one or more than one marker is a reflector of electromagnetic radiation. In one embodiment, one or more of the one or more than one marker emits or reflects electromagnetic radiation in the infrared wavelengths. In one embodiment, one or more of the one or more than one marker emits or reflects electromagnetic radiation in the ultraviolet wavelengths. In one embodiment, one or more of the one or more than one marker emits or reflects electromagnetic radiation in the visible wavelengths. In one embodiment, one or more of the one or more than one marker emits or reflects electromagnetic radiation in a first wavelength, range of wavelengths, group of wavelengths or group of ranges of wavelengths, and another of the one or more than one marker emits or reflects electromagnetic radiation in a second wavelength, range of wavelengths, group of wavelengths or group of ranges of wavelengths, where the first wavelength, range of wavelengths, group of wavelengths or group of ranges of wavelengths is different from the second wavelength, range of wavelengths, group of wavelengths or group of ranges of wavelengths.

According to another embodiment of the present invention, there is provided a system for determining or measuring temporomandibular joint positions and movements of a patient, the system comprising one or more than one mandibular/maxillary reference device according to the present invention. In one embodiment, the one or more than one mandibular/maxillary reference device is a plurality of mandibular/maxillary reference devices. In one embodiment, the plurality of mandibular/maxillary reference devices comprise mandibular/maxillary reference devices of at least two different sizes. In one embodiment, the system further comprises one or more than one upper face reference device for determining or measuring temporomandibular joint positions and movements of a patient, where the patient has a cranium with eyes, a nose with a bridge, and auricles with a superior aspect, the upper face reference device comprising a) a frontal section configured to fit over the eyes and the bridge of the nose of the patient, the frontal section comprising two lateral ends and a length 'l' between the two lateral ends, and a plane 'p' passing equidistantly between one lateral end of the frontal section and the other lateral end of the frontal section; b) two lateral sections, each lateral section configured to fit between the superior aspect of the auricle and the cranium of the patient, where each lateral section comprises an anterior end and a posterior end, where the anterior end of each lateral section is attached to one of the two lateral ends of the frontal section; and c) one or more than one marker attached to the frontal section, or to one or both of the lateral sections, or to both the frontal section and to one or both of the lateral sections. In one embodiment, the one or more than one upper face reference device is a plurality of upper face reference devices. In one embodiment, the plurality of upper face reference devices comprise upper face reference devices of at least two different sizes. In one embodiment, the one or more than one mandibular/maxillary reference device is a plurality of mandibular/maxillary reference devices. In one embodiment, the plurality of mandibular/maxillary reference devices comprise mandibular/maxillary reference devices of at least two different sizes. In one embodiment, the system further comprises a detecting device for detecting electromagnetic radiation and for converting the detected electromagnetic radiation to discrete or real time electronic or printed information. In one embodiment, the system further comprises a detecting device for detecting electromagnetic radiation and for converting the detected electromagnetic radiation to discrete or real time electronic or printed information. In one embodiment, the system further comprises a detecting device for detecting electromagnetic radiation and for converting the detected electromagnetic radiation to discrete or real time electronic or printed information. In one embodiment, the system further comprises a detecting device for detecting electromagnetic radiation and for converting the detected electromagnetic radiation to discrete or real time electronic or printed information. In one embodiment, the system further comprises an analyzer for processing information from a detecting device and for determining or measuring temporomandibular joint positions and movements of the patient using the information. In one embodiment, the detecting device and the analyzer are combined into one unit.

According to another embodiment of the present invention, there is provided a system for determining or measuring temporomandibular joint positions and movements of a patient, the system comprising one or more than one upper face reference device according to the present invention. In one embodiment, the one or more than upper face reference device is a plurality of upper face reference devices. In one embodiment, the plurality of upper face reference devices comprise upper face reference devices of at least two different sizes. In one embodiment, the system further comprises one or more than one mandibular/maxillary reference device for determining or measuring temporomandibular joint positions and movements of a patient, where the patient has a maxilla with an inferior anterior portion and a mandible with a superior anterior portion, the mandibular/maxillary reference device comprising: a) a mouthpiece configured to fit the inferior anterior portion of the maxilla of the patient or the superior anterior portion of the mandible of the patient, the mouthpiece comprising an anterior end and a posterior end; b) one or more than one support comprising a first posterior end, a second posterior end, an axial length ‘l’ from the first posterior end to the second posterior end, and one or more than one attachment position, where the one or more than one attachment element attaches the support to the mouthpiece at the one or more than one attachment position along the length ‘l’; c) one or more than one attachment element attaching the one or more than one support to the mouthpiece; and d) one or more than one marker attached to the one or more than one support. In one embodiment, the one or more than one mandibular/maxillary reference device is a plurality of mandibular/maxillary reference devices. In one embodiment, the plurality of mandibular/maxillary reference devices comprise interchangeable mandibular/maxillary reference of at least two different sizes. In one embodiment, the one or more than one upper face reference device is a plurality of upper face reference devices. In one embodiment, the plurality of upper face reference devices comprise upper face reference devices of at least two different sizes. In one embodiment, the system further comprises a detecting device for detecting electromagnetic radiation and for converting the detected electromagnetic radiation to discrete or real time electronic or printed information. In one embodiment, the system further comprises an analyzer for processing information from a detecting device and for determining or measuring temporomandibular joint positions and movements of the patient using the information. In one embodiment, the detecting device and the analyzer are combined into one unit.

According to another embodiment of the present invention, there is provided a method for determining or measuring one or more than one temporomandibular joint position or movement of a patient having an upper face, a maxilla with maxillary teeth, and a mandible with mandibular teeth. The method comprises a) providing a mandibular/maxillary reference device according to the present invention and applying the mandibular/maxillary reference device to the mandibular teeth of the patient; b) providing an upper face reference device according to the present invention and applying the upper face reference device to the upper face of the patient; c) reflecting electromagnetic radiation off of one or more than one of the one or more than one marker of the mandibular/maxillary reference device and one or more than one of the one or more than one marker of the upper face reference device, or emitting electromagnetic radiation from one or more than one of the one or more than one marker of the mandibular/maxillary reference device and one or more than one of the one or more than one marker of the upper face reference device, or both reflecting electromagnetic radiation off of one or more than one of the one or more than one marker of the mandibular/maxillary reference device and the one or more than one marker of the upper face reference device and emitting electromagnetic radiation from one or more than one of the one or more than one marker of the mandibular/maxillary reference device and the one or more than one marker of the upper face reference device; and d) providing a detecting device, and detecting the electromagnetic radiation reflected off of or emitted from the one or more than one marker of the mandibular/maxillary reference device and the one or more than one marker of the upper face reference device is detected by the detecting device, where the detecting device converts the detected electromagnetic radiation to discrete or real time electronic or printed information. In one embodiment, applying the mandibular/maxillary reference device comprises removably bonding the mandibular/maxillary reference device to the mandibular teeth of the patient. In one embodiment, the method further comprises recording the information by the detecting device. In one embodiment, the method further comprises transmitting the information by the detecting device to an analyzer. In one embodiment, the method further comprises processing the information transmitted by the detecting device by the analyzer, and determining values of one or more than one temporomandibular joint position or movement of the patient by the analyzer. In one embodiment, the method further comprises determining the values of one or more than one temporomandibular joint position or movement of the patient at a plurality of predetermined times. In one embodiment, the plurality of predetermined times is two times. In one embodiment, the plurality of predetermined times is three times. In one embodiment, the plurality of predetermined times is four times. In one embodiment, the plurality of predetermined times is more than four times. In one embodiment, the analyzer determines the values of one or more than one temporomandibular joint position or movement of the patient in real time. In one embodiment, the analyzer determines the values of one or more than one temporomandibular joint position or movement of the patient over a period of time. In one embodiment, the period of time is between 3 seconds and 3 minutes. In one embodiment, the analyzer determines the values of one or more than one temporomandibular joint position or movement of the patient in two dimensions. In one embodiment, the analyzer determines the values of one or more than one temporomandibular joint position or movement of the patient in three dimensions. In one embodiment, the analyzer comprises a display for displaying the information transmitted and the values of one or more than one temporomandibular joint position or movement of the patient, and the method further comprises displaying the information. In one embodiment, the method further comprises transmitting the values of one or more than one temporomandibular joint position or movement of the patient to a separate display by the analyzer, and displaying the values. In one embodiment, the method further comprises using the values to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment. In one embodiment, the markers on the mandibular/maxillary reference device are dissimilar to the markers on the upper face reference device. In one embodiment, the dissimilarity is selected from the group consisting of color, alignment, or emission or reflective characteristics.

According to another embodiment of the present invention, there is provided a method for determining or measuring one or more than one temporomandibular joint position or movement of a patient having an upper face, a maxilla with maxillary teeth, and a mandible with mandibular teeth. The method comprises a) providing a first mandibular/maxillary reference device according to the present invention and applying the first mandibular/maxillary reference device to the mandibular teeth of the patient; b) providing a second mandibular/maxillary reference device according to the present invention and applying the second mandibular/maxillary reference device to the maxillary teeth of the patient; c) reflecting electromagnetic radiation off of one or more than one of the one or more than one marker of the first mandibular/maxillary reference device and one or more than one of the one or more than one marker of the second mandibular/maxillary reference device, or emitting electromagnetic radiation from one or more than one of the one or more than one marker of the first mandibular/maxillary reference device and one or more than one of the one or more than one marker of the second mandibular/maxillary reference device, or both reflecting electromagnetic radiation off of one or more than one of the one or more than one marker of the first mandibular/maxillary reference device and the one or more than one marker of the second mandibular/maxillary reference device and emitting electromagnetic radiation from one or more than one of the one or more than one marker of the first mandibular/maxillary reference device and the one or more than one marker of the second mandibular/maxillary reference device; and d) providing a detecting device, and detecting the electromagnetic radiation reflected off of or emitted from the one or more than one marker of the first mandibular/maxillary reference device and the one or more than one marker of the second mandibular/maxillary reference device is detected by the detecting device, where the detecting device converts the detected electromagnetic radiation to discrete or real time electronic or printed information. In one embodiment, applying the first mandibular/maxillary reference device or applying the second mandibular/maxillary reference device comprises removably bonding the first mandibular/maxillary reference device to the mandibular teeth of the patient or removably bonding the second mandibular/maxillary reference device to the maxillary teeth of the patient. In one embodiment, the method further comprises recording the information by the detecting device. In one embodiment, the method further comprises transmitting the information by the detecting device to an analyzer. In one embodiment, the method further comprises processing the information transmitted by the detecting device by the analyzer, and determining values of one or more than one temporomandibular joint position or movement of the patient by the analyzer. In one embodiment, the method further comprises determining the values of one or more than one temporomandibular joint position or movement of the patient at a plurality of predetermined times. In one embodiment, the plurality of plurality of predetermined times is two times. In one embodiment, the plurality of plurality of predetermined times is three times. In one embodiment, the plurality of plurality of predetermined times is four times. In one embodiment, the plurality of plurality of predetermined times is more than four times. In one embodiment, the analyzer determines the values of one or more than one temporomandibular joint position or movement of the patient in real time. In one embodiment, the analyzer determines the values of one or more than one temporomandibular joint position or movement of the patient over a period of time. In one embodiment, the period of time is between 3 seconds and 3 minutes. In one embodiment, the analyzer determines the values of one or more than one temporomandibular joint position or movement of the patient in two dimensions. In one embodiment, the analyzer determines the values of one or more than one temporomandibular joint position or movement of the patient in three dimensions. In one embodiment, the analyzer comprises a display for displaying the information transmitted and the values of the values of one or more than one temporomandibular joint position or movement of the patient, and the method further comprises displaying the information. In one embodiment, the method further comprises transmitting the values of one or more than one temporomandibular joint position or movement of the patient to a separate display by the analyzer, and displaying the values. In one embodiment, the method further comprises using the values to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment. In one embodiment, the markers on the first mandibular/maxillary reference device are dissimilar to the markers on the second mandibular/maxillary reference device. In one embodiment, the dissimilarity is selected from the group consisting of color, alignment, or emission or reflective characteristics. In one embodiment, the upper face of the patient has an auriculo-orbital plane (Frankfurt plane), and where the method further comprises determining the variance of the first mandibular/maxillary reference device applied to the mandibular teeth of the patient from the auriculo-orbital plane of the patient. In one embodiment, determining the variance of the first mandibular/maxillary reference device applied to the mandibular teeth of the patient from the auriculo-orbital plane of the patient comprises: a) applying an upper face reference device comprising markers to the patient, where the positions of the markers on the upper face reference device are used to indicate the auriculo-orbital plane, and applying a mandibular/maxillary reference device to the maxillary teeth of the patient; b) determining the variance between the auriculo-orbital plane as indicated by the position of the markers on the upper face reference device and mandibular/maxillary reference device applied to the maxillary teeth; c) removing the upper face reference device while leaving the mandibular/maxillary reference device as the second mandibular/maxillary reference device for the method of determining or measuring one or more than one temporomandibular joint position or movement of a patient; and d) using the variance in determining or measuring one or more than one temporomandibular joint position or movement of the patient. In one embodiment, determining the variance of the first mandibular/maxillary reference device applied to the mandibular teeth of the patient from the auriculo-orbital plane of the patient comprises: a) applying a mandibular/maxillary reference device comprising markers to the mandibular teeth; b) applying a mandibular/maxillary reference device to the maxillary teeth of the patient; c) having the patient occlude the maxillary teeth and mandibular teeth creating an occlusion plane as represented by the markers on the mandibular/maxillary reference device on the mandibular teeth; d) assuming the variance between the auriculo-orbital plane and the occlusion plane is a known deviation; e) determining the variance between the auriculo-orbital plane and mandibular/maxillary reference device applied to the maxillary teeth using the assumed variance; f) removing the mandibular/maxillary reference device from the mandibular teeth while leaving the mandibular/maxillary reference device applied to the maxillary teeth as the second mandibular/maxillary reference device for the method of determining or measuring one or more than one temporomandibular joint position or movement of a patient; and g) using the variance between the auriculo-orbital plane and mandibular/maxillary reference device applied to the maxillary teeth in determining or measuring one or more than one temporomandibular joint position or movement of the patient. In one embodiment, the mandibular/maxillary reference device applied to the mandibular teeth comprises a mouthpiece is an occlusal plane indexing plate. In one embodiment, the known deviation between the auriculo-orbital plane and the occlusion plane is between 8° and 10°.

According to another embodiment of the present invention, there is provided a method of diagnosing a condition or disease of the temporomandibular joint of a patient. The method comprises a) identifying a patient with a potential temporomandibular joint condition or disease; b) determining or measuring values for one or more than one temporomandibular joint position or movement of the patient according to the present invention; and c) using the values for the one or more than one temporomandibular joint position or movement of the patient to diagnose the condition or disease of the temporomandibular joint of the patient or the lack of a condition or disease of the temporomandibular joint of the patient.

According to another embodiment of the present invention, there is provided a method of treating a condition or disease of the temporomandibular joint of a patient. The method comprises a) diagnosing a condition or disease of the temporomandibular joint of a patient according to the present invention; and b) treating the patient.

DRAWINGS

These and other features, aspects and advantages of the present invention will become better understood with regard to the following description, appended claims, and accompanying drawings where:

Figure 38:
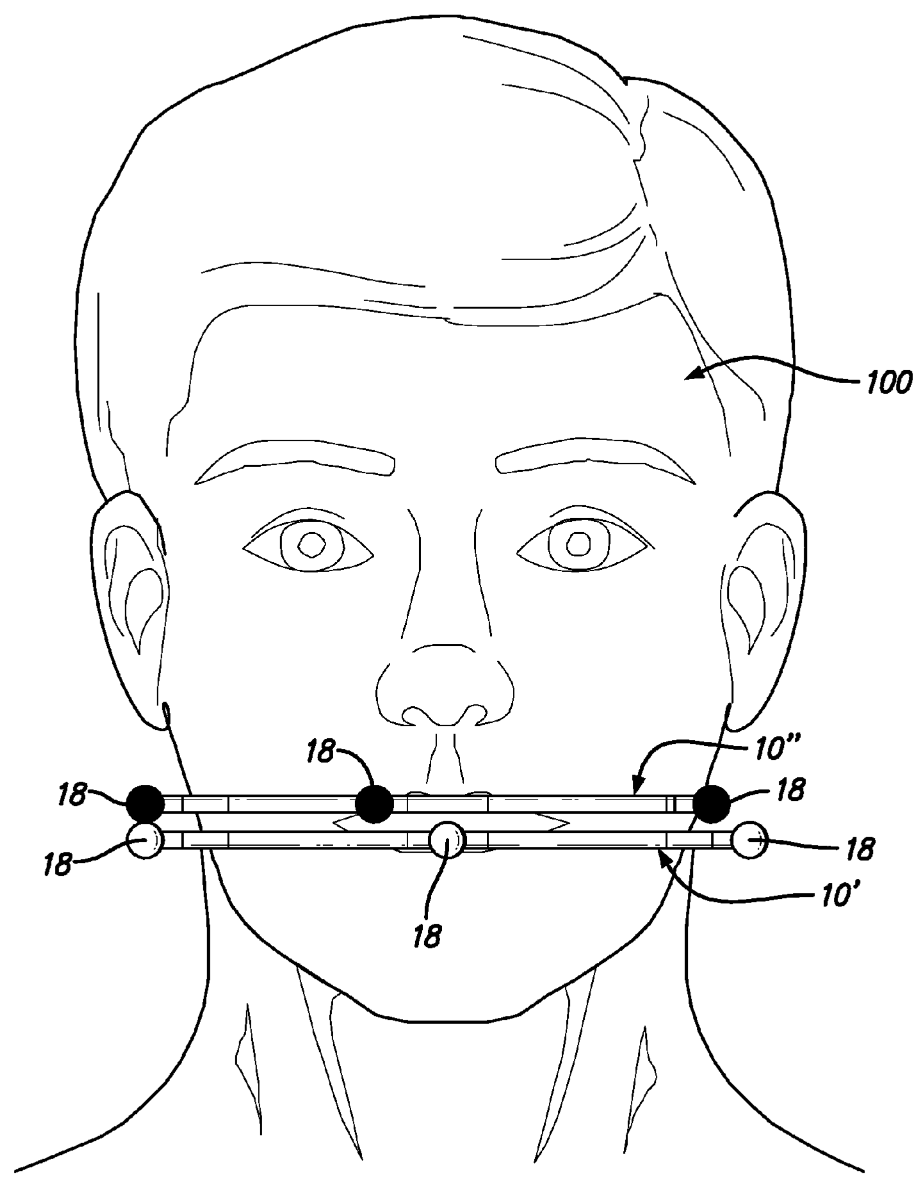
Figure 39:
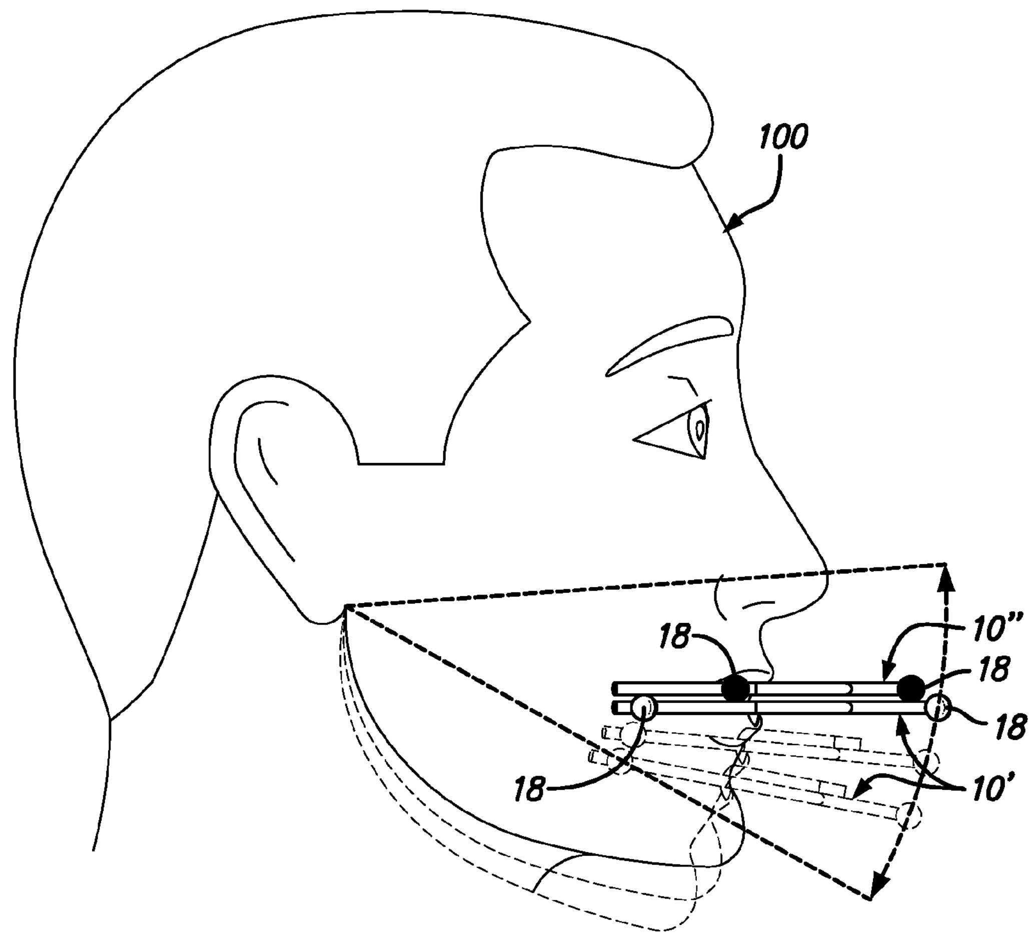
Figure 40:
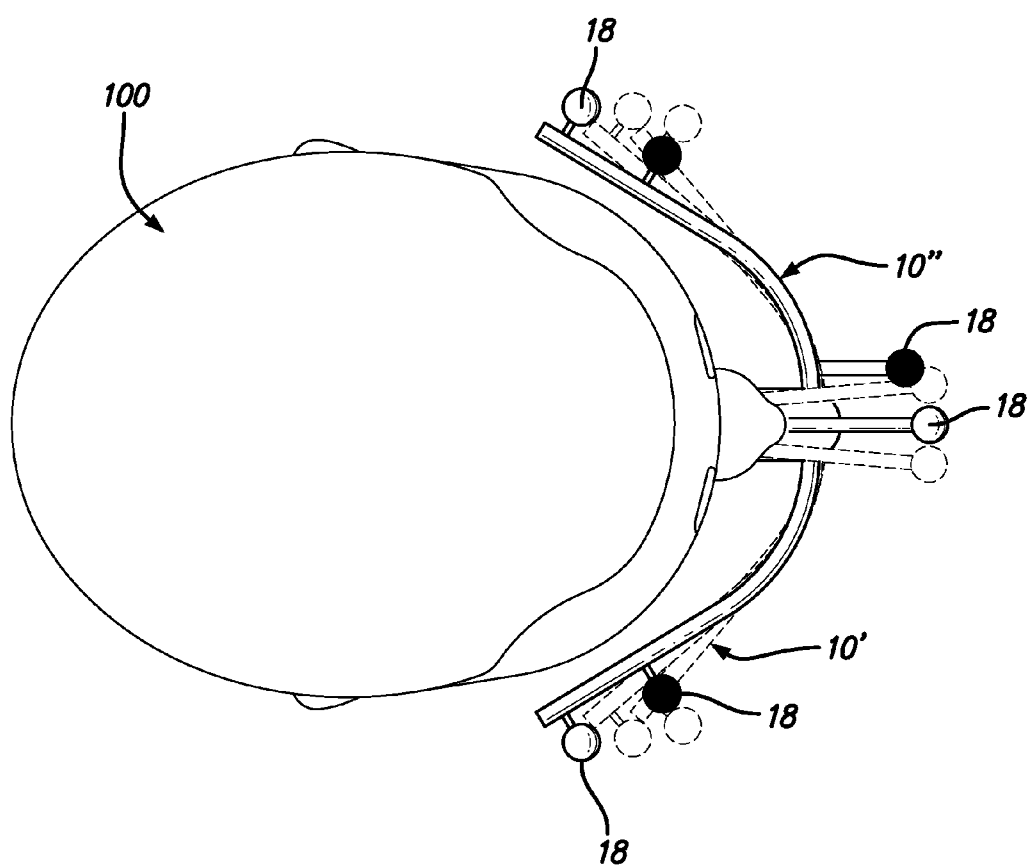
Figure 41:
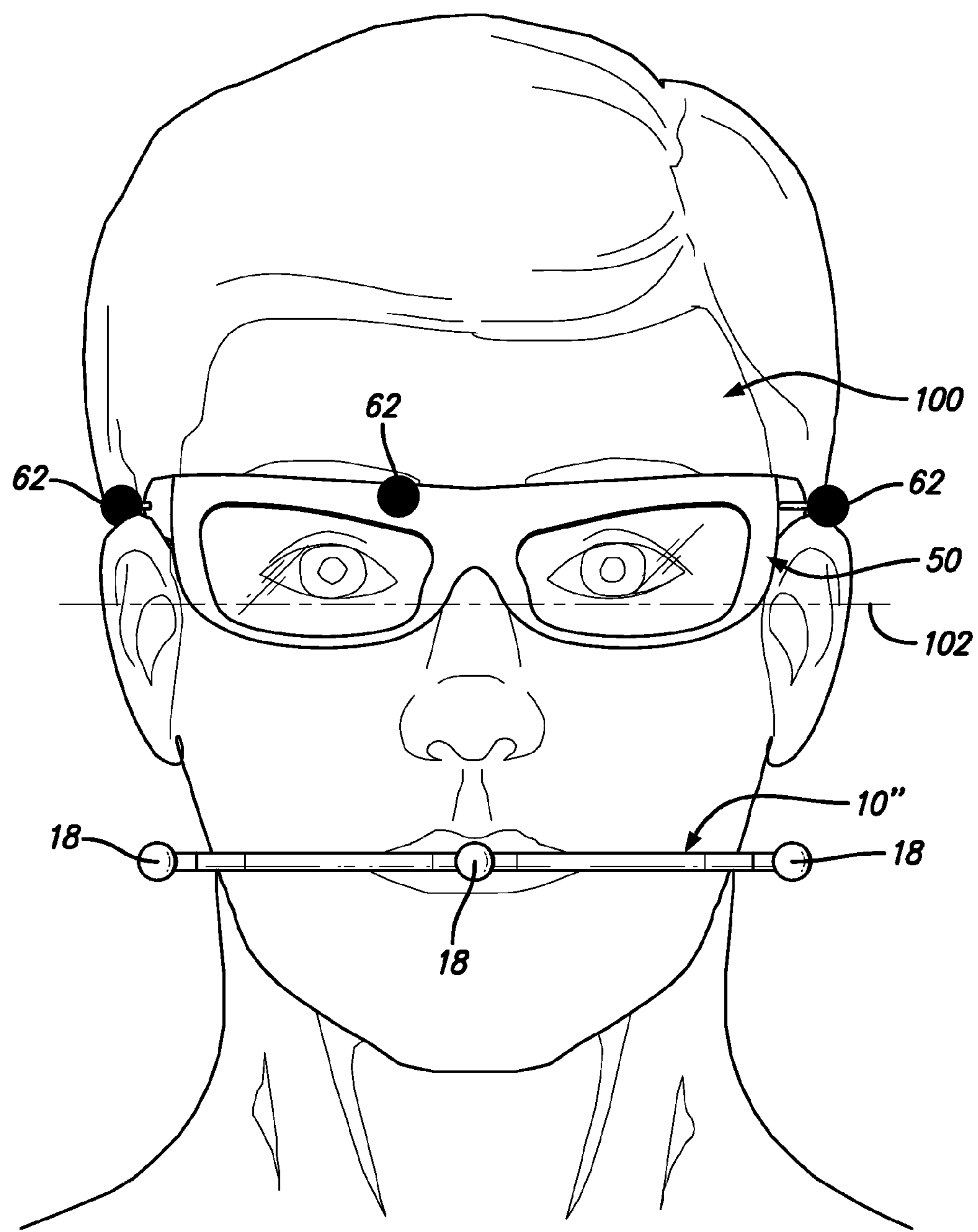
Figure 42:
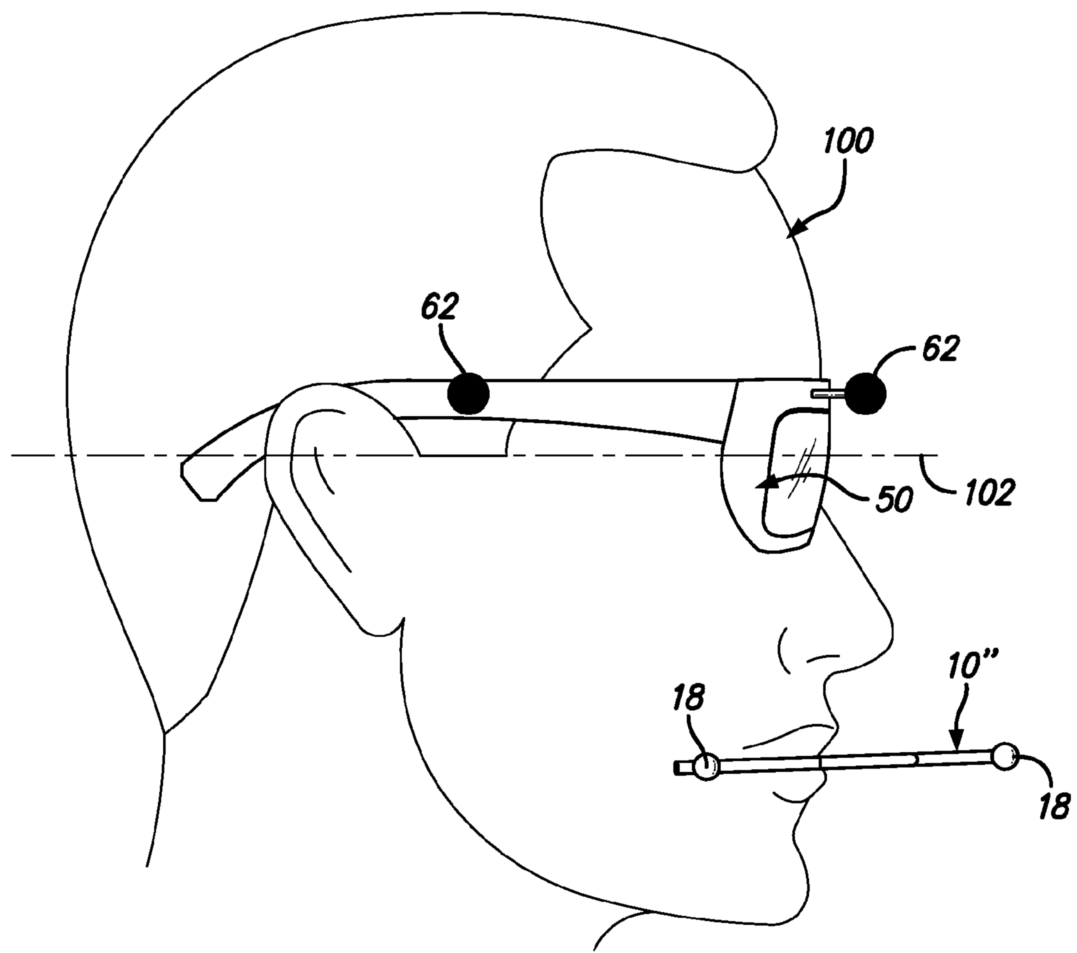
Figure 43:
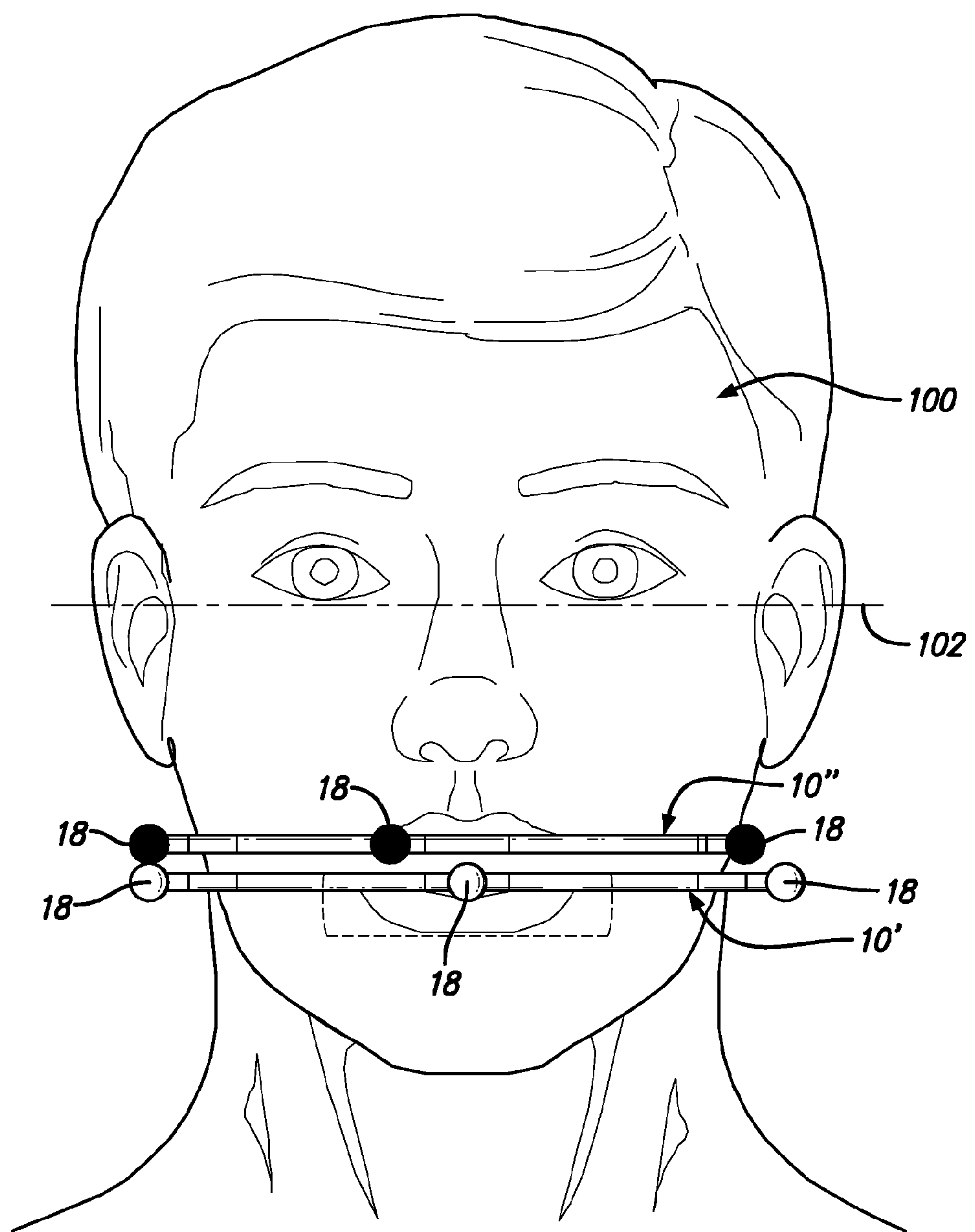
Figure 44:
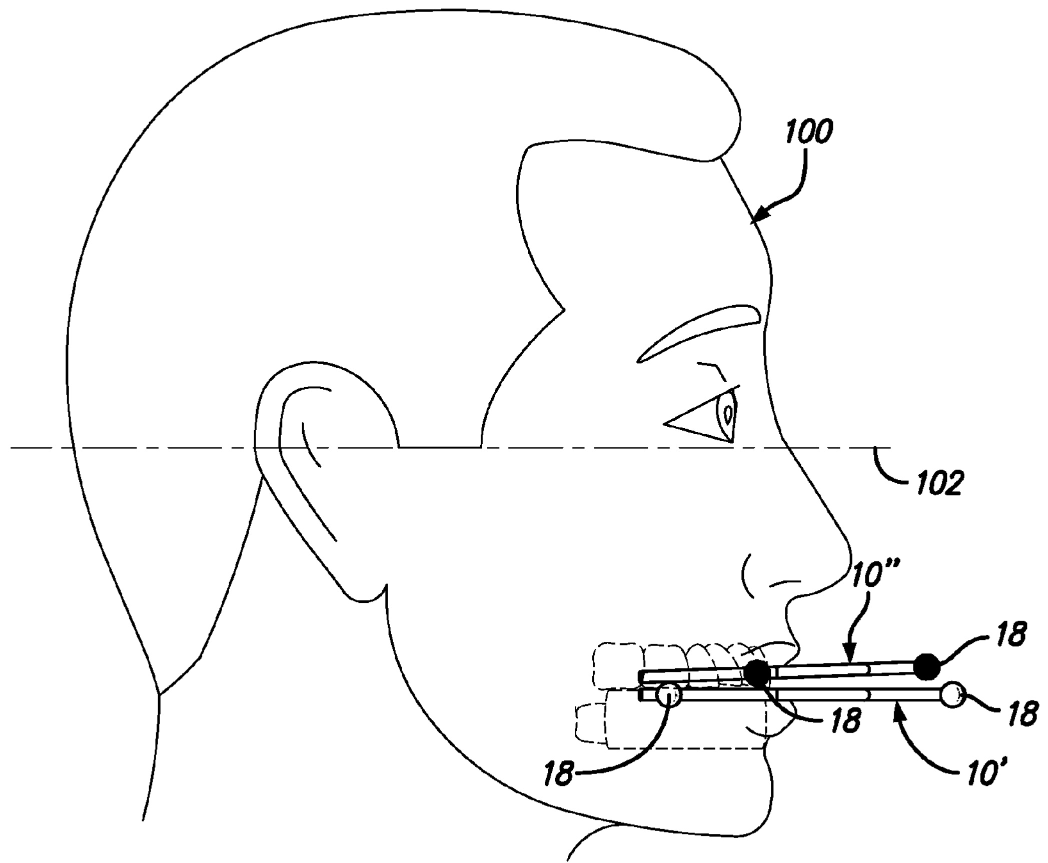

FIG. 38 is a schematic frontal perspective view of the head of a patient with a first mandibular/maxillary reference device according to the present invention applied to the maxilla of the patient and a second mandibular/maxillary reference device according to the present invention applied to the mandible of the patient with the mandible moving from a first position to two other positions (shown in broken lines);

FIG. 39 is a schematic lateral perspective view of the head of the patient as shown in FIG. 38;

FIG. 40 is a schematic top perspective view of the head of the patient as shown in FIG. 38;

FIG. 41 is a schematic frontal perspective view of the head of a patient with an upper face reference device according to the present invention applied to the upper face of the patient and a mandibular/maxillary reference device according to the present invention applied to the maxilla of the patient;

FIG. 42 is a schematic lateral perspective view of the head of the patient as shown in FIG. 41;

FIG. 43 is a schematic frontal perspective view of the head of a patient with a first mandibular/maxillary reference device according to the present invention applied to the maxilla of a patient and a second mandibular/maxillary reference device according to the present invention applied to the mandible of the patient; and FIG. 44 is a schematic lateral perspective view of the head of the patient as shown in FIG. 43.

DESCRIPTION

According to one embodiment of the present invention, there is provided a device for determining or measuring temporomandibular joint positions and movements of a patient. In one embodiment, the device is a mandibular/maxillary reference device. In another embodiment, the device is an upper face reference device. According to another embodiment of the present invention, there is provided a system for determining or measuring temporomandibular joint positions and movements of a patient, where the system comprises one or more than one device according to the present invention for determining or measuring temporomandibular joint positions and movements of a patient. According to another embodiment of the present invention, there is provided a method for determining or measuring one or more than one temporomandibular joint position or movement of a patient. The method comprises providing a device according to the present invention or providing a system according to the present invention and using the device or using the system to determine or measure one or more than one temporomandibular joint position or movement of the patient. The method is both faster and less expensive than currently used methods, and is suitable for use on every patient. The method is capable of determining or measuring temporomandibular joint positions and movements of a patient in three-dimensions, that is, positions and movements of the mandible of the patient relative to the cranium of the patient, including all three-dimensional rotations and translations of the mandible relative to the cranium. According to another embodiment of the present invention, there is provided a method of diagnosing a condition or disease of a temporomandibular joint of a patient. The method of diagnosing comprises determining or measuring one or more than one temporomandibular joint position or movement according to the present invention, and using the one or more than one determined or measured position or movement to diagnose the condition or disease of the temporomandibular joint of the patient. According to another embodiment of the present invention, there is provided a method of treating a condition or disease of a temporomandibular joint of a patient. The method comprises diagnosing a condition or disease of a temporomandibular joint of a patient according to the present invention, and then treating the condition or disease of the temporomandibular joint of the patient. The device, system and methods will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, two elements of a device are "integral" if they are joined together in a manner that does not allow separation of the two elements from one another by the user of the device without cutting through one or both of the elements, or destroying the function one or both of the two elements, or of the device as a whole.

All dimensions specified in this disclosure are by way of example only and are not intended to be limiting. Further, the proportions shown in these Figures are not necessarily to scale. As will be understood by those with skill in the art with reference to this disclosure, the actual dimensions and proportions of any device, any system, any part of a device or any part of a system disclosed in this disclosure will be determined by its intended use.

The device and the system of the present invention and their component parts can be constructed according to standard techniques, as will be understood by those with skill in the art with reference to this disclosure.

As used in this disclosure, except where the context requires otherwise, the method steps disclosed and shown are not intended to be limiting nor are they intended to indicate that each step is essential to the method or that each step must occur in the order disclosed.

As used in this disclosure, "determining or measuring one or more than one temporomandibular joint position or movement of a patient" and similar phrases means "determining, measuring or both determining and measuring one or more than one temporomandibular joint position, one or more than one temporomandibular joint movement, or both one or more than one temporomandibular joint position and one or more than one temporomandibular joint movement of a patient."

According to one embodiment of the present invention, there is provided a device for determining or measuring temporomandibular joint positions and movements of a patient.

Figure 1:
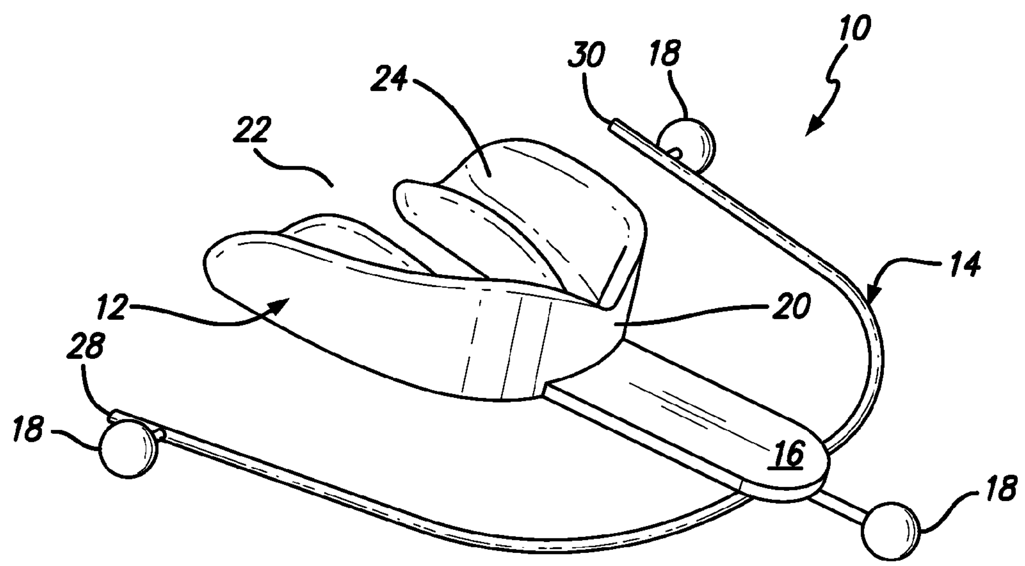
FIG. 1 is a superior, lateral, frontal perspective view of a device for determining or measuring temporomandibular joint positions and movements of a patient according to the present invention.
Figure 2:
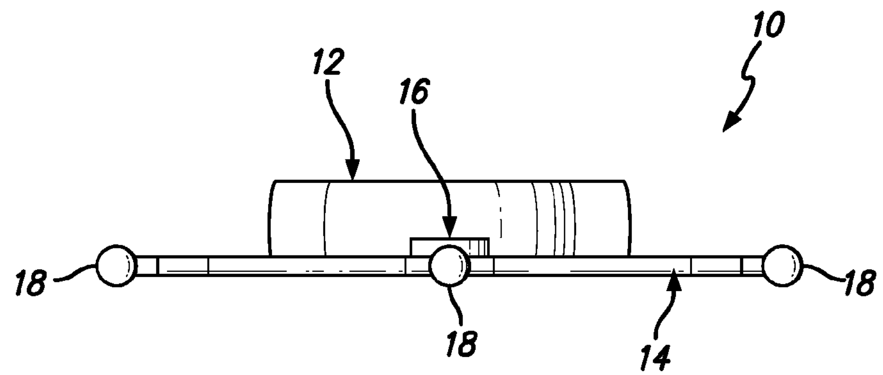
FIG. 2 is a frontal perspective view of the device shown in FIG. 1.
Figure 3:
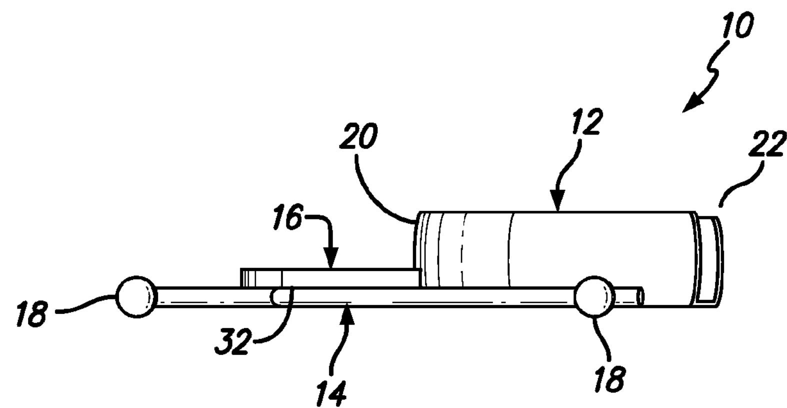
FIG. 3 is a lateral perspective view of the device shown in FIG. 1.
Figure 4:
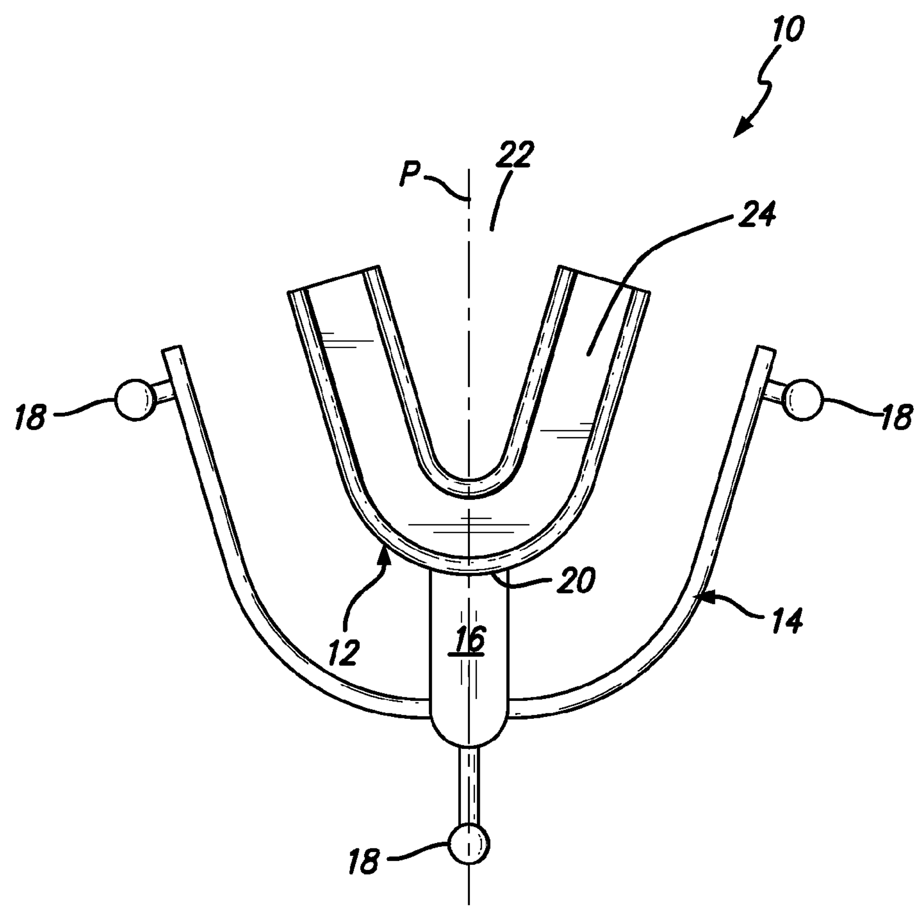
FIG. 4 is a top perspective view of the device shown in FIG. 1.
Figure 5:
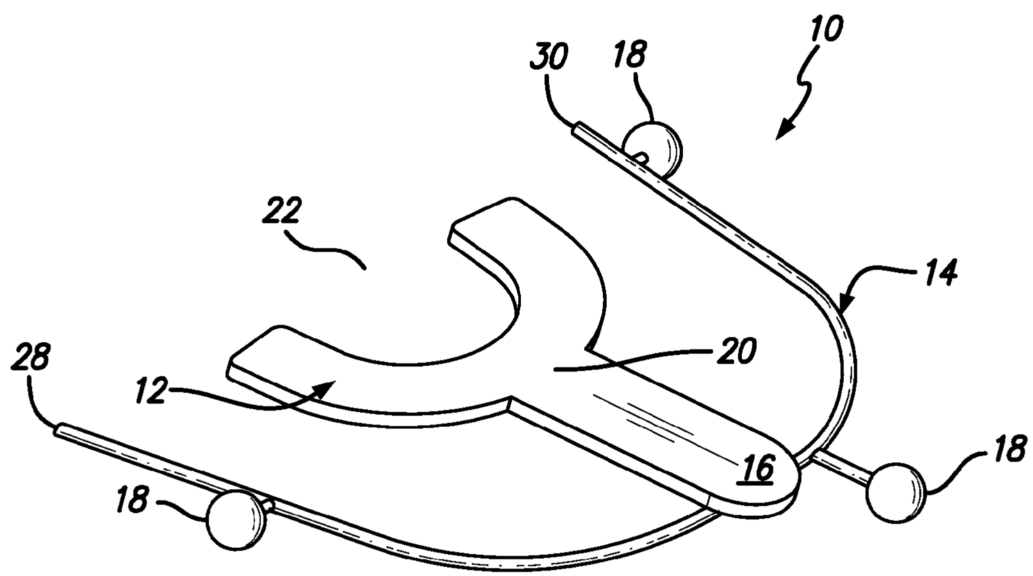
FIG. 5 is a superior, lateral, frontal perspective view of another embodiment of another device for determining or measuring temporomandibular joint positions and movements of a patient according to the present invention.
Figure 6:
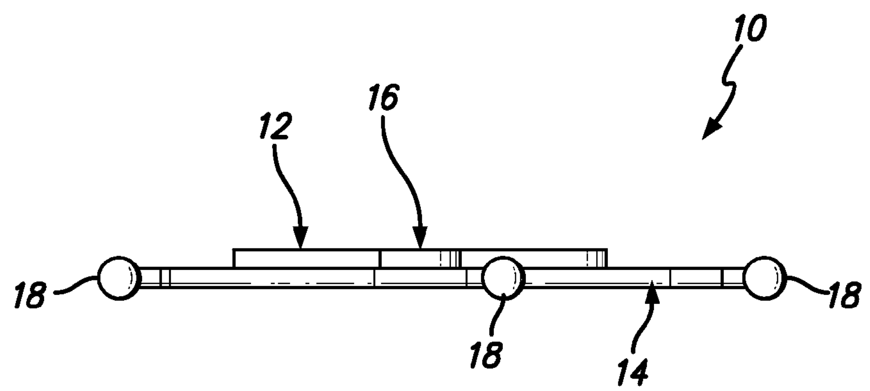
FIG. 6 is a frontal perspective view of the device shown in FIG. 5.
Figure 7:
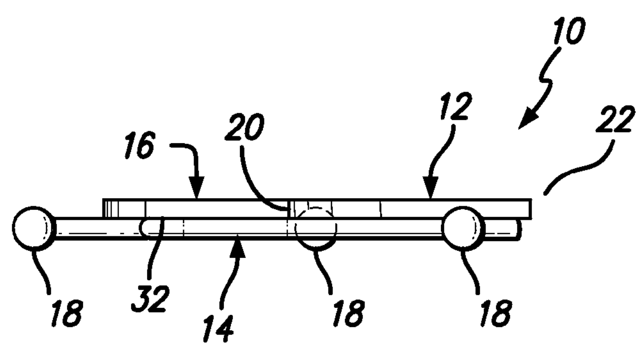
FIG. 7 is a lateral perspective view of the device shown in FIG. 5.
Figure 8:
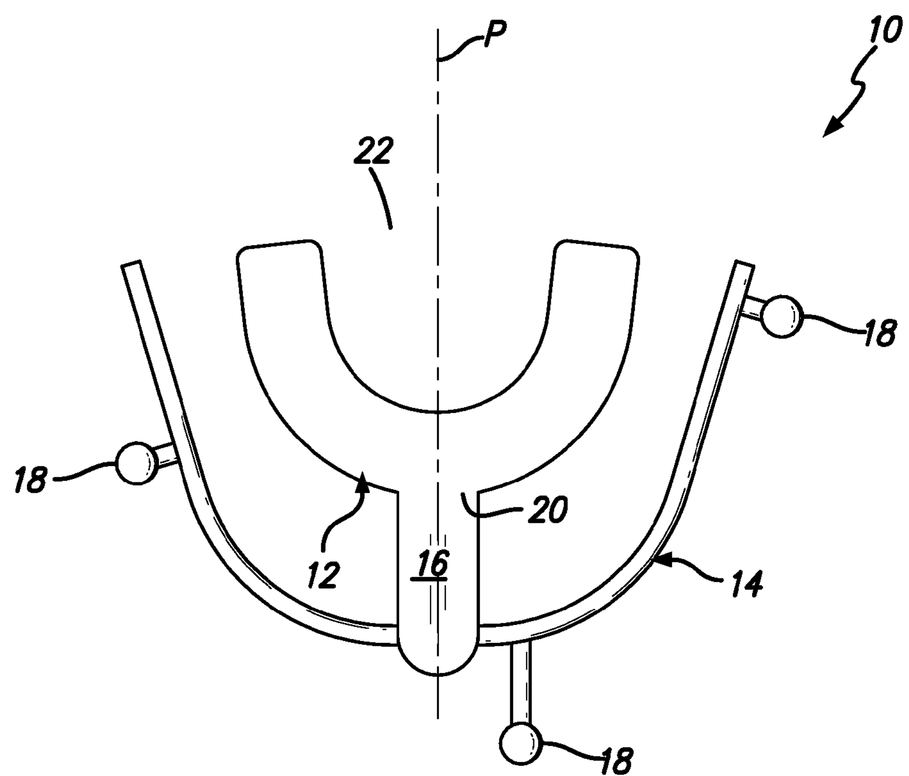
FIG. 8 is a top perspective view of the device shown in FIG. 5.
Figure 9:
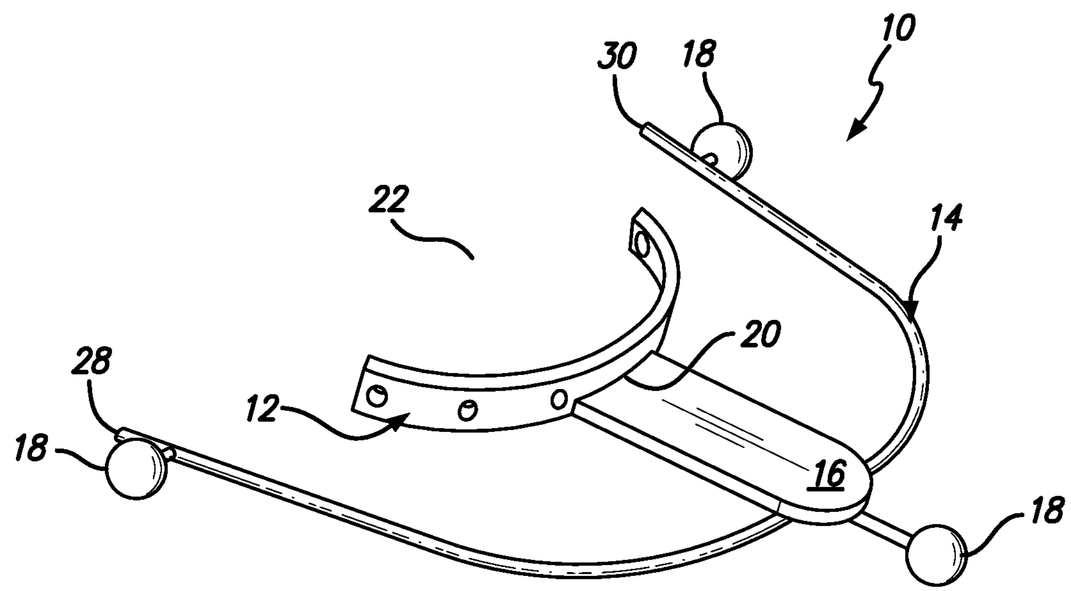
FIG. 9 is a superior, lateral, frontal perspective view of another embodiment of another device for determining or measuring temporomandibular joint positions and movements of a patient according to the present invention.
Figure 10:
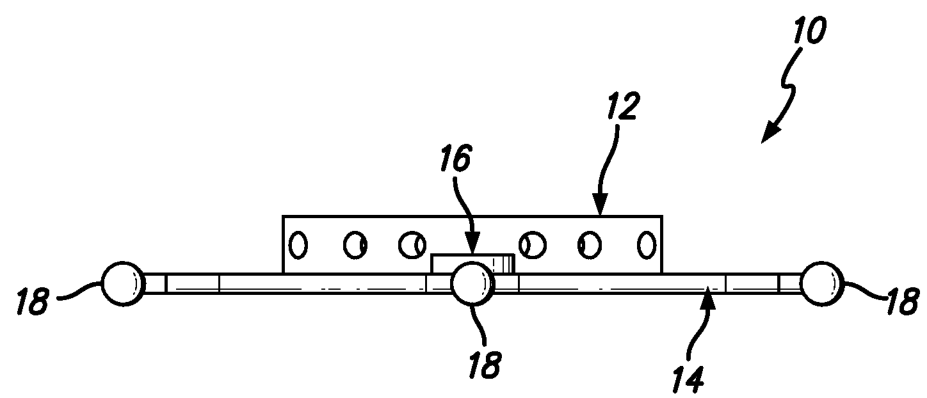
FIG. 10 is a frontal perspective view of the device shown in FIG. 9.
Figure 11:
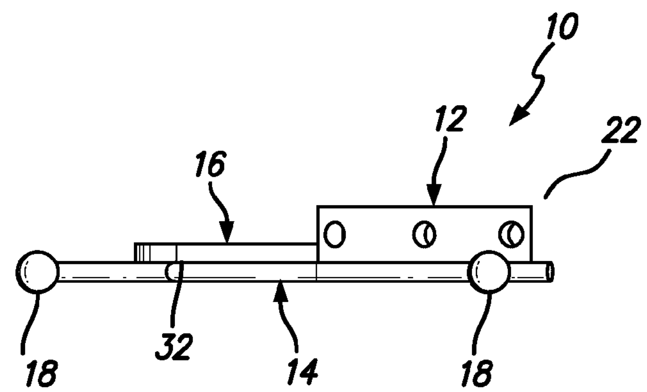
FIG. 11 is a lateral perspective view of the device shown in FIG. 9.
Figure 12:
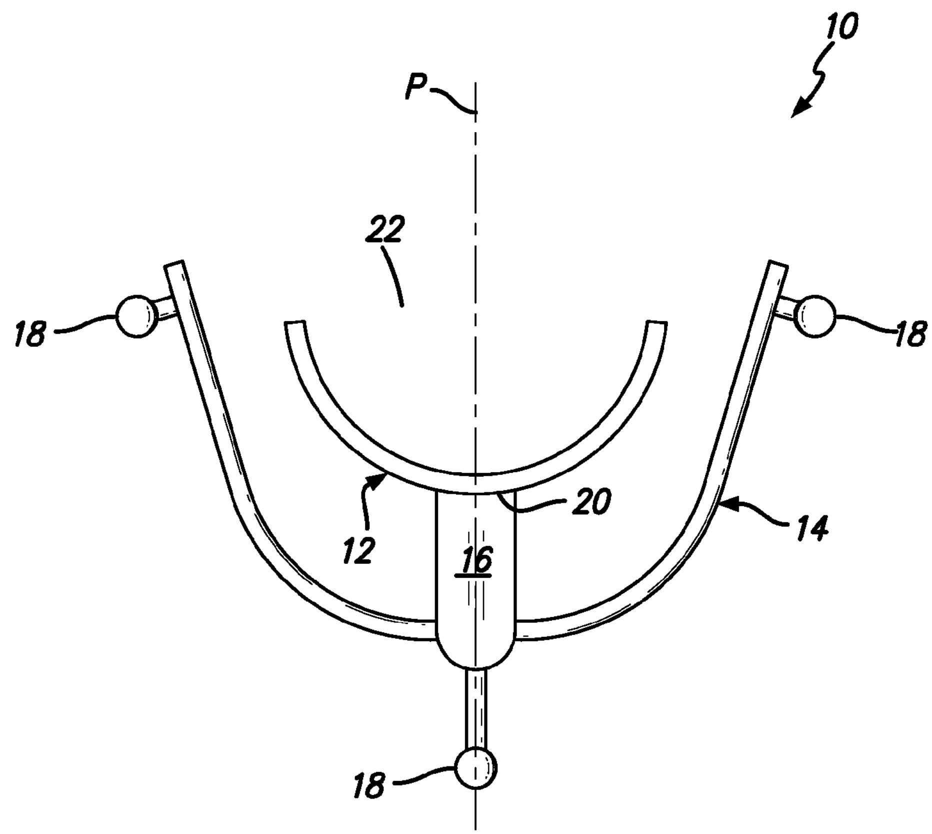
FIG. 12 is a top perspective view of the device shown in FIG. 9.
Figure 13:
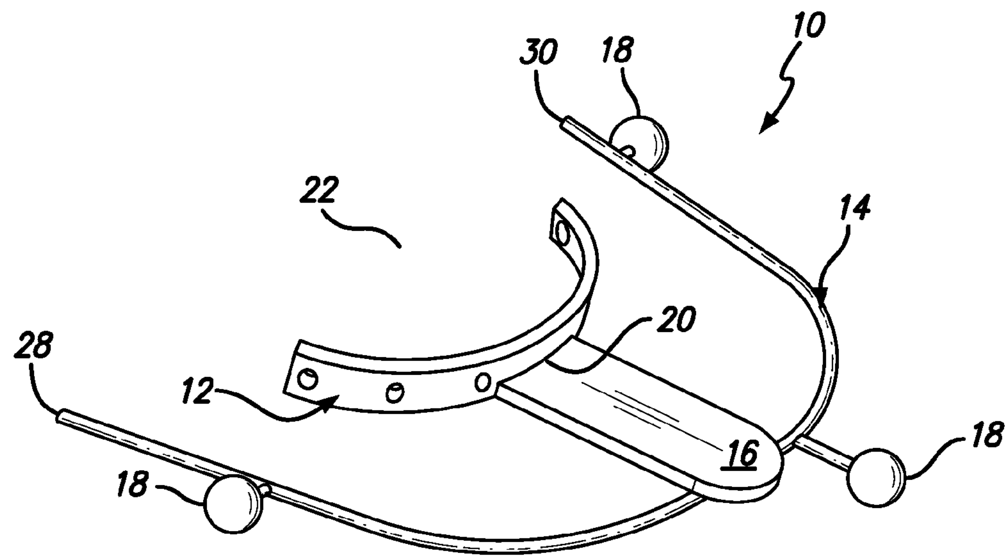
FIG. 13 is a superior, lateral, frontal perspective view of another embodiment of another device for determining or measuring temporomandibular joint positions and movements of a patient according to the present invention.
Figure 14:
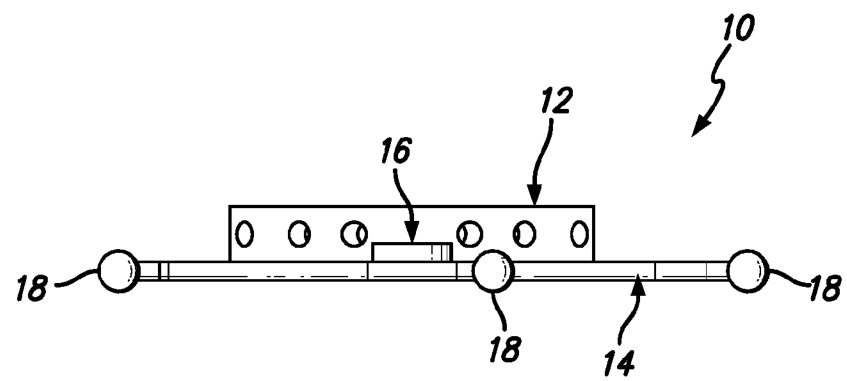
FIG. 14 is a frontal perspective view of the device shown in FIG. 13.
Figure 15:
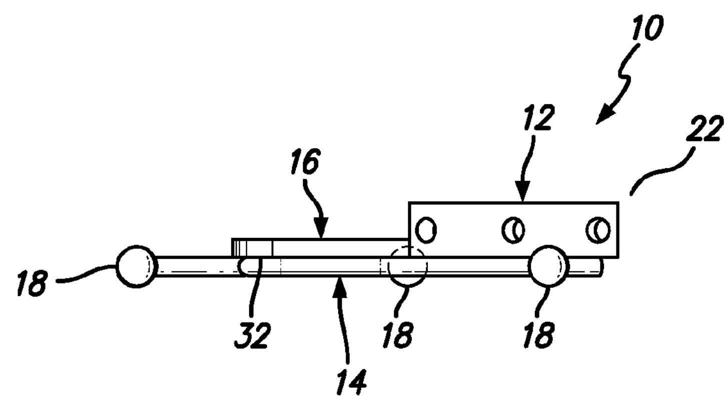
FIG. 15 is a lateral perspective view of the device shown in FIG. 13.
Figure 16:
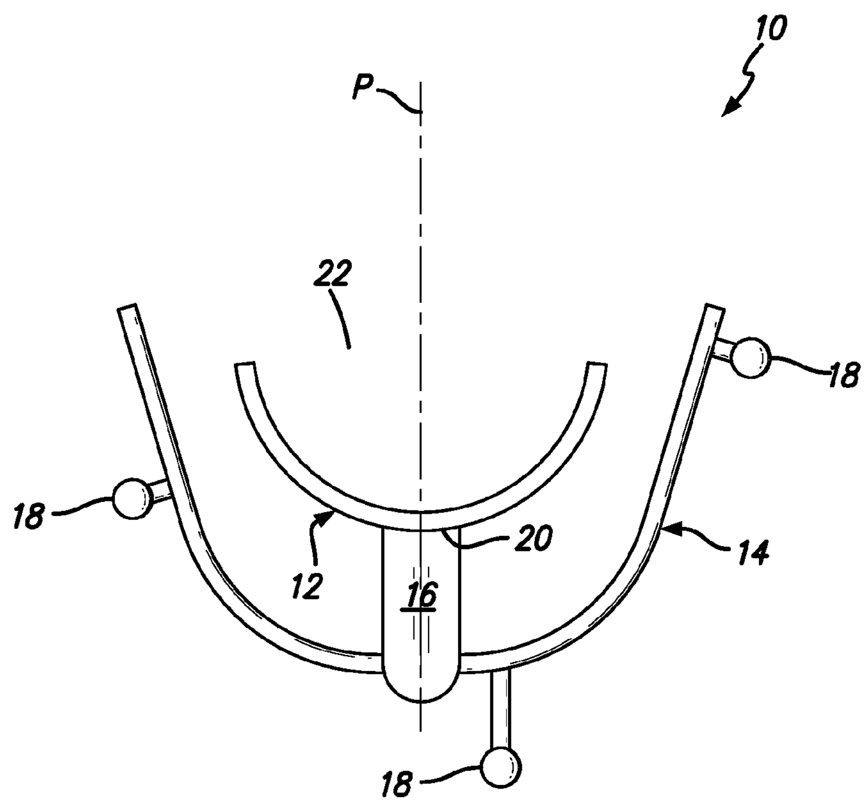
FIG. 16 is a top perspective view of the device shown in FIG. 13.
Figure 17:
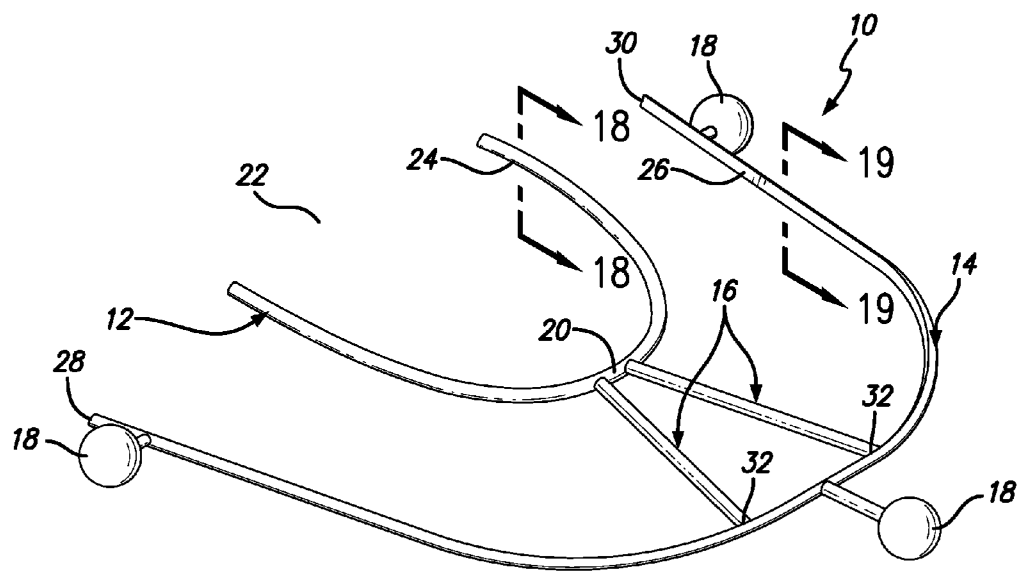
FIG. 17 is a superior, lateral, frontal perspective view of another embodiment of another device for determining or measuring temporomandibular joint positions and movements of a patient according to the present invention.
Figure 18:
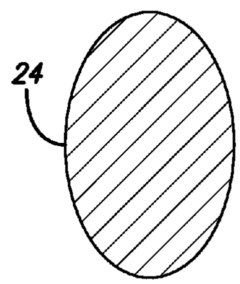
FIG. 18 is a cross-sectional view of the mouthpiece of the device shown in FIG. 17 taken along the line 18-18.
Figure 19:
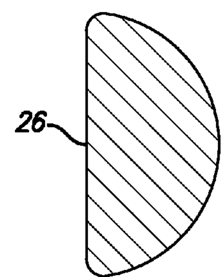
FIG. 19 is a cross-sectional view of the support of the device shown in FIG. 17 taken along the line 19-19.
Figure 20:
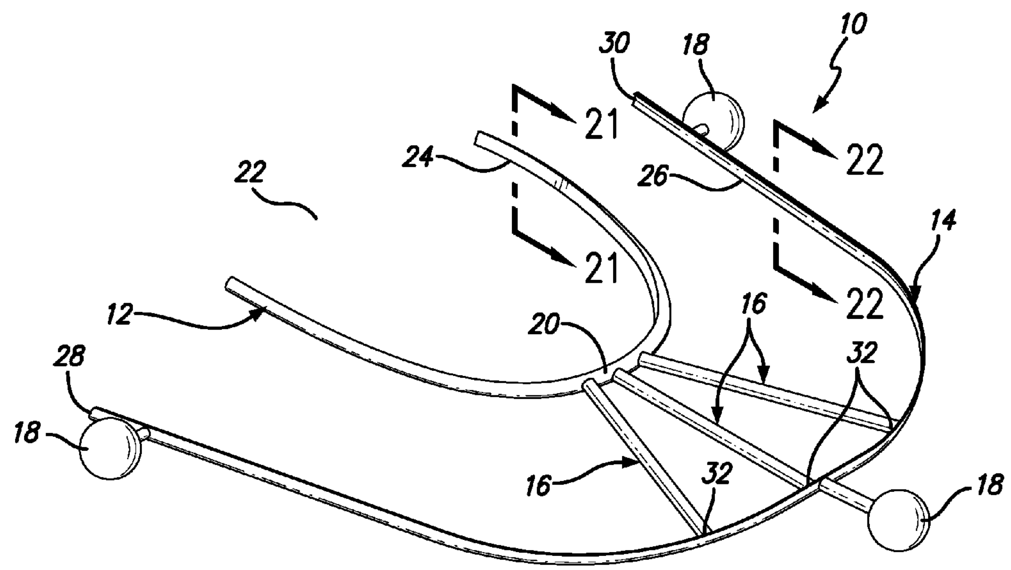
FIG. 20 is a superior, lateral, frontal perspective view of another embodiment of another device for determining or measuring temporomandibular joint positions and movements of a patient according to the present invention.
Figure 21:
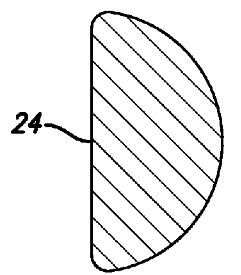
FIG. 21 is a cross-sectional view of the mouthpiece of the device shown in FIG. 20 taken along the line 21-21.
Figure 22:
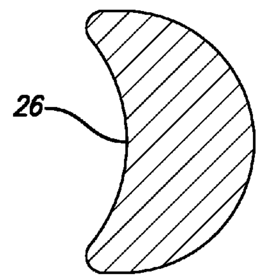
FIG. 22 is a cross-sectional view of the support of the device shown in FIG. 20 taken along the line 22-22.
Figure 23:
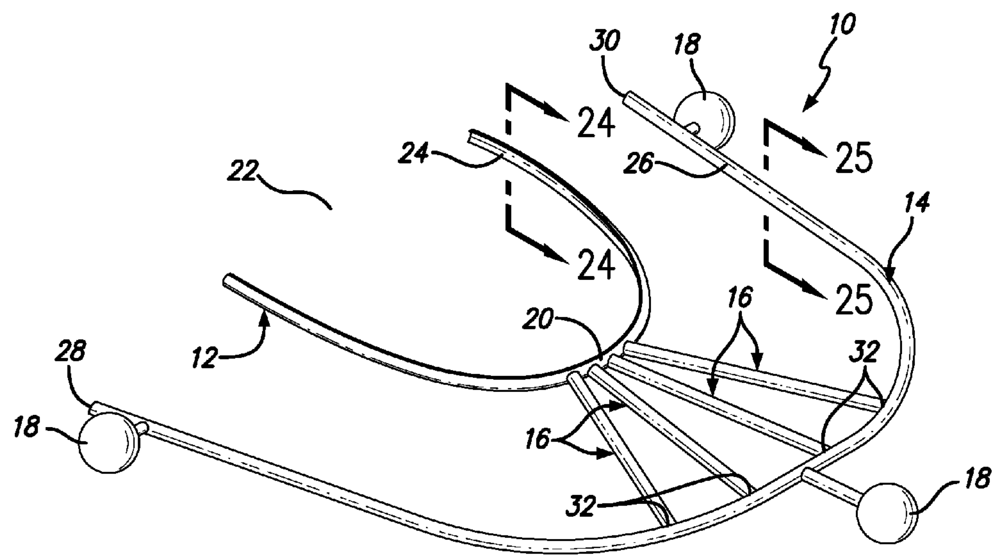
FIG. 23 is a superior, lateral, frontal perspective view of another embodiment of another device for determining or measuring temporomandibular joint positions and movements of a patient according to the present invention.
Figure 24:
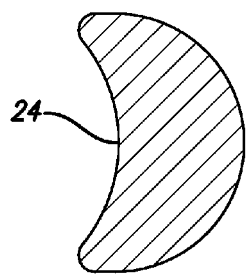
FIG. 24 is a cross-sectional view of the mouthpiece of the device shown in FIG. 23 taken along the line 24-24.
Figure 25:
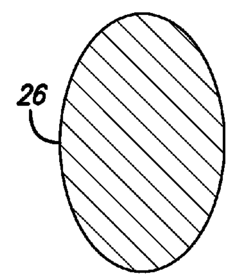
FIG. 25 is a cross-sectional view of the support of the device shown in FIG. 23 taken along the line 25-25.
Figure 26:
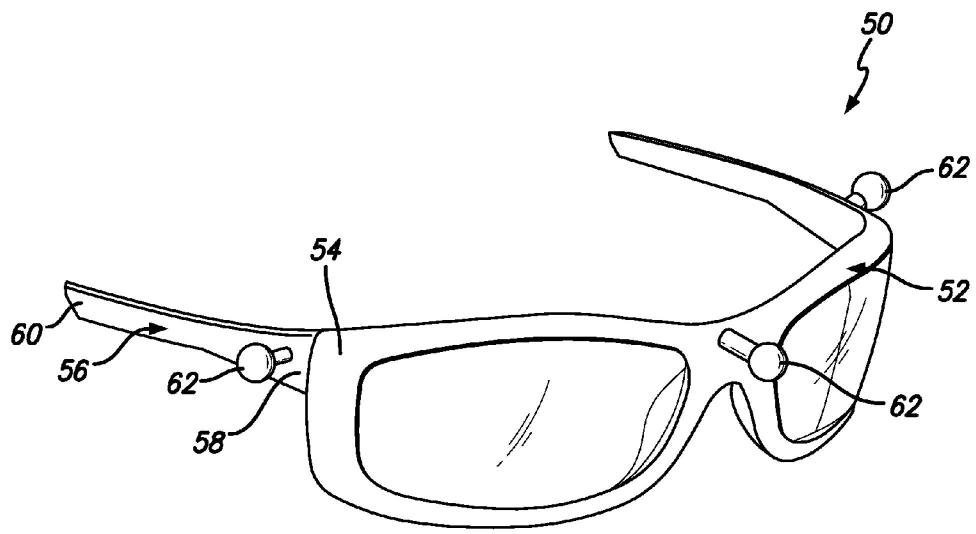
FIG. 26 is a superior, lateral, frontal perspective view of another device for determining or measuring temporomandibular joint positions and movements of a patient according to the present invention.
Figure 27:
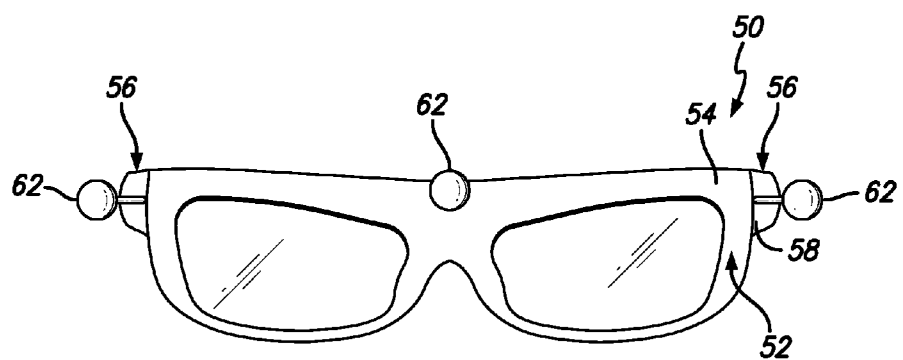
FIG. 27 is a frontal perspective view of the device shown in FIG. 26.
Figure 28:
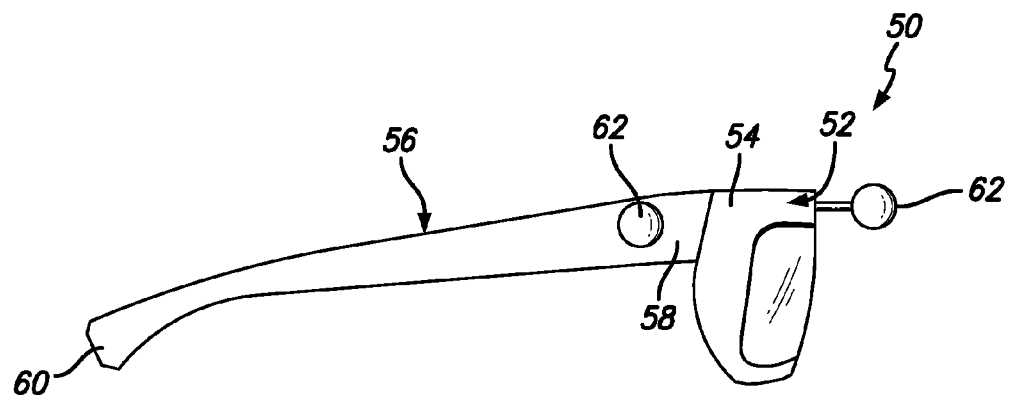
FIG. 28 is a lateral perspective view of the device shown in FIG. 26.

Referring now to FIG. 1 through FIG. 25 there are shown, respectively, a superior, lateral, frontal perspective view of a device for determining or measuring temporomandibular joint positions and movements of a patient according to the present invention (FIG. 1), a frontal perspective view of the device shown in FIG. 1 (FIG. 2), a lateral perspective view of the device shown in FIG. 1 (FIG. 3), a top perspective view of the device shown in FIG. 1 (FIG. 4), a superior, lateral, frontal perspective view of another embodiment of another device for determining or measuring temporomandibular joint positions and movements of a patient according to the present invention (FIG. 5), a frontal perspective view of the device shown in FIG. 5 (FIG. 6), a lateral perspective view of the device shown in FIG. 5 (FIG. 7), a top perspective view of the device shown in FIG. 5 (FIG. 8), a superior, lateral, frontal perspective view of another embodiment of another device for determining or measuring temporomandibular joint positions and movements of a patient according to the present invention (FIG. 9), a frontal perspective view of the device shown in FIG. 9 (FIG. 10), a lateral perspective view of the device shown in FIG. 9 (FIG. 11), a top perspective view of the device shown in FIG. 9 (FIG. 12), a superior, lateral, frontal perspective view of another embodiment of another device for determining or measuring temporomandibular joint positions and movements of a patient according to the present invention (FIG. 13), a frontal perspective view of the device shown in FIG. 13 (FIG. 14), a lateral perspective view of the device shown in FIG. 13 (FIG. 15), a top perspective view of the device shown in FIG. 13 (FIG. 16), a superior, lateral, frontal perspective view of another embodiment of another device for determining or measuring temporomandibular joint positions and movements of a patient according to the present invention (FIG. 17), a cross-sectional view of the mouthpiece of the device shown in FIG. 17 taken along the line 18-18 (FIG. 18), a cross-sectional view of the support of the device shown in FIG. 17 taken along the line 19-19 (FIG. 19), a superior, lateral, frontal perspective view of another embodiment of another device for determining or measuring temporomandibular joint positions and movements of a patient according to the present invention (FIG. 20), a cross-sectional view of the mouthpiece of the device shown in FIG. 20 taken along the line 21-21 (FIG. 21), a cross-sectional view of the support of the device shown in FIG. 20 taken along the line 22-22 (FIG. 22), a superior, lateral, frontal perspective view of another embodiment of another device for determining or measuring temporomandibular joint positions and movements of a patient according to the present invention (FIG. 23), a cross-sectional view of the mouthpiece of the device shown in FIG. 23 taken along the line 24-24 (FIG. 24), and a cross-sectional view of the support of the device shown in FIG. 23 taken along the line 25-25 (FIG. 25). As shown in FIG. 1 through FIG. 25, in one embodiment, the device 10 for determining or measuring temporomandibular joint positions and movements of a patient according to the present invention is a mandibular/maxillary reference device 10, and comprises a mouthpiece 12, one or more than one support 14, one or more than one attachment element 16 attaching the one or more than one support 14 to the mouthpiece 12, and one or more than one marker 18 attached to the one or more than one support 14. The mouthpiece 12 comprises an anterior end 20 and a posterior end 22 which correspond to the anterior and posterior of the maxilla and mandible of the patient when the mandibular/maxillary reference device 10 is applied to the patient, and a plane 'p' passing from the anterior end 20 of the mouthpiece 12 to the posterior end 22 of the mouthpiece 12. In a preferred embodiment, the mouthpiece 12 is symmetric about the plane 'p,' as shown most clearly in FIG. 4, FIG. 8, FIG. 12 and FIG. 16, which corresponds to the sagittal plane of the patient when the mandibular/maxillary reference device 10 is applied to the patient. In one embodiment, the mouthpiece 12 is configured to fit the inferior anterior portion of the maxilla of the patient or the superior anterior portion of the mandible of the patient. In a preferred embodiment, the mouthpiece 12 is configured to interchangeably and reversibly fit both the inferior anterior portion of the maxilla of the patient and the superior anterior portion of the mandible of the patient by rotating the mandibular/maxillary reference device 10 around an axis passing from the anterior end 20 of the mouthpiece 12 to the posterior end 22 of the mouthpiece 12 in plane 'p' as will be understood by those with skill in the art with respect to this disclosure. In one embodiment, as shown in FIG. 1, FIG. 2, FIG. 3 and FIG. 4, the mouthpiece 12 is a dental tray. In another embodiment, as shown in FIG. 5, FIG. 6, FIG. 7 and FIG. 8, the mouthpiece 12 is an occlusal plane indexing plate. In another embodiment, as shown in FIGS. 9-17, 20 and 23, the mouthpiece 12 is a curved bracket configured to engage only facial and buccal surfaces of maxillary teeth or mandibular teeth of the patient thereby permitting the patient full occlusion when the mandibular/maxillary reference device 10 is applied to the patient. In one embodiment, the curved bracket comprises a longitudinal cross-section and the longitudinal cross-section is rectangular, such as for example the buccal indexing fork shown in FIG. 9 through FIG. 16. In another embodiment, the curved bracket comprises a longitudinal cross-section and the longitudinal cross-section is round. In another embodiment, as shown in FIG. 17 and FIG. 18, the curved bracket comprises a longitudinal cross-section and the longitudinal cross-section is oval. In another embodiment, as shown in FIG. 20 and FIG. 21, the curved bracket comprises a longitudinal cross-section with a central surface 24 and the central surface 24 is flat. In another embodiment, as shown in FIG. 23 and FIG. 24, the curved bracket comprises a longitudinal cross-section with a central surface 24 and the central surface 24 is concave. In one embodiment, the mouthpiece 12 is custom made to fit the patient. In another embodiment, the mouthpiece 12 is selected from a group of standardized sizes available as part of a system according to the present invention to fit the patient. In one embodiment, the mouthpiece 12 is integrally attached to the attachment element 16. In another embodiment, the mouthpiece 12 is reversibly attached to the attachment element 16, such as for example by a male-female connector, by a magnet or by a screw mechanism, thereby allowing replacement of one mouthpiece 12 for another mouthpiece 12 on the mandibular/maxillary reference device 10 during use, such as for example to obtain a better fit for the mandibular/maxillary reference device 10, or to change the size of the mouthpiece 12, or to sterilize the mouthpiece 12 separately from the remainder of the mandibular/maxillary reference device 10, as will be understood by those with skill in the art with respect to this disclosure.

The mandibular/maxillary reference device 10 further comprises one or more than one support 14 and one or more than one attachment element 16 attaching the support 14 to the mouthpiece 12. The support 14 can be any suitable shape for the intended purpose, as will be understood by those with skill in the art with respect to this disclosure. In one embodiment, the support 14 is a curved bracket. In one embodiment, the curved bracket comprises a longitudinal cross-section and the longitudinal cross-section is round, as shown in FIG. 1 through FIG. 16. In another embodiment, as shown in FIG. 17 and FIG. 19, the curved bracket comprises a longitudinal cross-section with an inner surface 26 and the inner surface 26 is flat to increase comfort of the patient when the mandibular/ maxillary reference device 10 is applied to the patient. In another embodiment, as shown in FIG. 20 and FIG. 22, the curved bracket comprises a longitudinal cross-section with an inner surface 26 and the inner surface 26 is concave to increase comfort of the patient when the mandibular/maxillary reference device 10 is applied to the patient. In another embodiment, as shown in FIG. 23 and FIG. 25, the curved bracket comprises a longitudinal cross-section and the longitudinal cross-section is oval to increase comfort of the patient when the mandibular/maxillary reference device 10 is applied to the patient. The support 14 further comprises a first posterior end 28, a second posterior end 30, an axial length 'l' from the first posterior end 28 to the second posterior end 30, and one or more than one attachment position 32, where the one or more than one attachment element 16 attaches the support 14 to the mouthpiece 12 at the one or more than one attachment position 32 along the length 'l,' where "attachment position" is understood to be a continuous discrete length along the axial length 'l,' such as for example 1 mm, 3 mm, 5 mm or 10 mm. In one embodiment, the one or more than one attachment position 32 is one attachment position 32 coinciding with the plane 'p,' as shown most clearly in FIG. 3, FIG. 4, FIG. 7, FIG. 8, FIG. 11, FIG. 12, FIG. 15 and FIG. 16. In another embodiment, the one or more than one attachment position 32 is two attachment positions 32 as shown in FIG. 17. In another embodiment, the one or more than one attachment position 32 is three attachment positions 32 as shown in FIG. 20. In another embodiment, the one or more than one attachment position 32 is four attachment positions 32 as shown in FIG. 23. The number and configuration of the one or more than one attachment position 32 can however be any suitable number and configuration for the intended purpose, as will be understood by those with skill in the art with respect to this disclosure.

The mandibular/maxillary reference device 10 further comprises one or more than one attachment element 16 attaching the support 14 to the mouthpiece 12. The one or more than one attachment element 16 can be any shape suitable for the intended purpose of attaching the mouthpiece 12 to the support 14 during use of the mandibular/maxillary reference device 10, as will be understood by those with skill in the art with respect to this disclosure. In one embodiment, one of the one or more than one attachment element 16 is a flat plate, as shown most clearly in FIG. 1, FIG. 4, FIG. 5, FIG. 8, FIG. 9, FIG. 12, FIG. 13 and FIG. 16. In another embodiment, one of the one or more than one attachment element 16 is a tubular strut, as shown in FIG. 17, FIG. 20 and FIG. 23. In one embodiment, the one or more than one attachment element 16 is one attachment element 16 as seen in FIG. 1 through FIG. 16. In another embodiment, the one or more than one attachment element 16 is two attachment elements 16 as seen in FIG. 17. In another embodiment, the one or more than one attachment element 16 is three attachment elements 16 as seen in FIG. 20. In another embodiment, the one or more than one attachment element 16 is four attachment elements 16 as seen in FIG. 23. However, the number of attachment elements 16 and their arrangement can be any suitable number and arrangement for the intended purpose of attaching the mouthpiece 12 to the support 14 during use of the mandibular/maxillary reference device 10, as will be understood by those with skill in the art with respect to this disclosure. In one embodiment, the attachment element 16 is integrally attached to the support 14. In another embodiment, the attachment element 16 is reversibly attached to the support 14, such as for example by a male-female connector, by a magnet or by a screw mechanism, thereby allowing replacement of one support 14 for another support 14 on the mandibular/maxillary reference device 10 during use, such as for example to change the location or function of one or more than one marker 18, or to change the size of the support 14, or to sterilize the support 14 separately from the remainder of the mandibular/maxillary reference device 10, as will be understood by those with skill in the art with respect to this disclosure.

The mandibular/maxillary reference device 10 further comprises one or more than one marker 18. The number and position of the markers 18 depends on the temporomandibular joint positions and movements being determined or measured by the mandibular/maxillary reference device 10 and the method according to the present invention, as will be understood by those with skill in the art with respect to this disclosure. In one embodiment, the one or more than one marker 18 of the mandibular/maxillary reference device 10 is two markers 18. In another embodiment, the one or more than one marker 18 of the mandibular/maxillary reference device 10 is three markers 18. In another embodiment, the one or more than one marker 18 of the mandibular/maxillary reference device 10 is four markers 18. In another embodiment, the one or more than one marker 18 of the mandibular/maxillary reference device 10 is more than four markers 18. In one embodiment, as shown most clearly in FIG. 1, FIG. 2, FIG. 4, FIG. 9, FIG. 10 and FIG. 12, one marker 18 is attached to the support 14 coincident with the plane 'p.' In another embodiment, as shown most clearly in FIG. 5, FIG. 6, FIG. 8, FIG. 13, FIG. 14 and FIG. 16, none of the one or more than one marker 18 is attached to the support 14 coincident with the plane 'p.' In one embodiment, as shown most clearly in FIG. 1, FIG. 4, FIG. 9 and FIG. 12, the mandibular/maxillary reference device 10 comprises a plurality of markers 18, and two of the plurality of markers 18 are positioned equidistantly from plane 'p' along the axial length 'l' of the support 14. In another embodiment, as shown most clearly in FIG. 5, FIG. 8, FIG. 13 and FIG. 16, the mandibular/maxillary reference device 10 comprises a plurality of markers 18, and two of the plurality of markers 18 are positioned non-equidistantly from plane 'p' along the axial length 'l' of the support 14. In one embodiment, as shown most clearly in FIG. 1, FIG. 4, FIG. 9, FIG. 12, FIG. 17, FIG. 20 and FIG. 23, the mandibular/maxillary reference device 10 comprises a plurality of markers 18, and two of the plurality of markers 18 are positioned equidistantly from plane 'p' along the axial length 'l' of the support 14, and another marker 18 is attached to the support 14 coincident wit*h the plane 'p.'

In one embodiment, all of the one or more than one markers 18 are integrally and non-movably attached to the support 14. In another embodiment, one or more of the one or more than one marker 18 is movably attached to the support 14. In another embodiment, all of the one or more than one markers 18 are movably attached to the support 14. In another embodiment, one or more of the one or more than one marker 18 is removably attached to the support 14. In another embodiment, all of the one or more than one markers 18 are removably attached from the support 14.

In one embodiment, one or more of the one or more than one marker 18 is an emitter of electromagnetic radiation. In another embodiment, all of the one or more than one markers 18 are emitters of electromagnetic radiation. In one embodiment, one or more of the one or more than one marker 18 is a reflector of electromagnetic radiation. In another embodiment, all of the one or more than one markers 18 are reflectors of electromagnetic radiation. In one embodiment, one or more of the one or more than one marker 18 is an emitter of electromagnetic radiation, and one or more of the one or more than one marker 18 is a reflector of electromagnetic radiation. The one or more than one marker 18 can emit or reflect electromagnetic radiation in any suitable wavelength, range of wavelengths, group of wavelengths or group of ranges of wavelengths, as will be understood by those with skill in the art with respect to this disclosure. In one embodiment, one or more of the one or more than one marker 18 emits or reflects electromagnetic radiation in the infrared wavelengths. In another embodiment, one or more of the one or more than one marker 18 emits or reflects electromagnetic radiation in the ultraviolet wavelengths. In a preferred embodiment, one or more of the one or more than one marker 18 emits or reflects electromagnetic radiation in the visible wavelengths. In one embodiment, one or more of the one or more than one marker 18 emits or reflects electromagnetic radiation in a first wavelength, range of wavelengths, group of wavelengths or group of ranges of wavelengths, and another of the one or more than one marker 18 emits or reflects electromagnetic radiation in a second wavelength, range of wavelengths, group of wavelengths or group of ranges of wavelengths, where the first wavelength, range of wavelengths, group of wavelengths or group of ranges of wavelengths is different from the second wavelength, range of wavelengths, group of wavelengths or group of ranges of wavelengths which advantageously allows distinction between the markers 18 based on the wavelength, range of wavelengths, group of wavelengths or group of ranges of wavelengths emitted or reflected.

Figure 33:
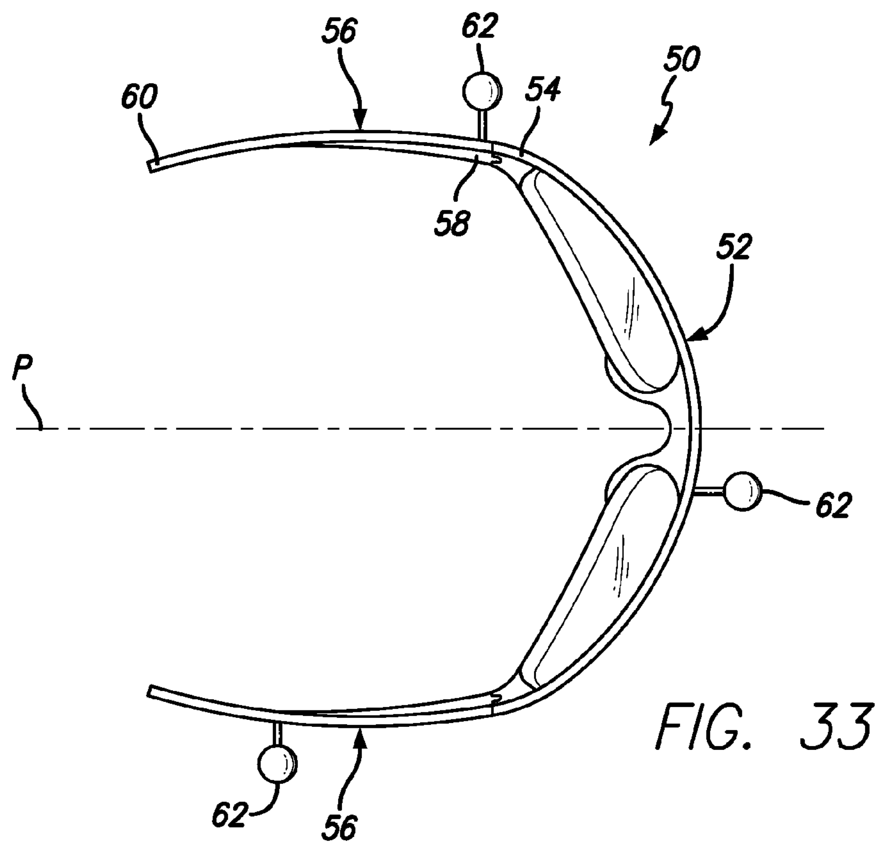
FIG. 33 is a top perspective view of the device shown in FIG. 30.

According to another embodiment of the present invention, there is provided another device for determining or measuring temporomandibular joint positions and movements of a patient. Referring now to FIG. 26 through FIG. 33, there are shown, respectively, a superior, lateral, frontal perspective view of another device for determining or measuring temporomandibular joint positions and movements of a patient according to the present invention (FIG. 26), a frontal perspective view of the device shown in FIG. 26 (FIG. 27), a lateral perspective view of the device shown in FIG. 26 (FIG. 28), a top perspective view of the device shown in FIG. 26 (FIG. 29), a superior, lateral, frontal perspective view of another embodiment of a device for determining or measuring temporomandibular joint positions and movements of a patient according to the present invention (FIG. 30), a frontal perspective view of the device shown in FIG. 30 (FIG. 31), a lateral perspective view of the device shown in FIG. 30 (FIG. 32), and a top perspective view of the device shown in FIG. 30 (FIG. 33). As shown in FIG. 26 through FIG. 33, in one embodiment, the device 50 for determining or measuring temporomandibular joint positions and movements of a patient according to the present invention is an upper face reference device, and comprises a frontal section 52 comprising two lateral ends 54, a length 'l' between the two lateral ends 54, and a plane 'p' passing equidistantly between one lateral end of the frontal section and the other lateral end of the frontal section, which corresponds to the sagittal plane of the patient when the upper face reference device 50 is applied to the patient. The upper face reference device 50 further comprises two lateral sections 56, where each lateral section comprises an anterior end 58 and a posterior end 60. The anterior end 58 of each lateral section 56 is attached to one of the two lateral ends 54 of the frontal section 52. In one embodiment, the anterior end 58 of each lateral section 56 is attached to one of the two lateral ends 54 of the frontal section 52 by a hinge mechanism allowing movement of the posterior end 60 of one lateral section 56 closer to and farther from the posterior end 60 of the other lateral section 56. The frontal section 52 is configured to fit over the eyes and the bridge of the nose of a patient when the upper face reference device 50 is applied to the patient. The lateral sections 56 are configured to fit between the superior aspect of the auricle (pinna) and the cranium of a patient when the upper face reference device 50 is applied to the patient. In a preferred embodiment, the frontal section 52 and lateral sections 56 of the upper face reference device 50 are a frame of a pair of eyeglasses, with or without lenses, where the frontal section 52 is an eyepiece of a frame of the pair of eyeglasses and the lateral sections 56 are temples of the frame of the pair of eyeglasses.

The upper face reference device 50 further comprises one or more than one marker 62 attached to the frontal section 52, or to one or both of the lateral sections 56, or to both the frontal section 52 and to one or both of the lateral sections 56. The number and position of the markers 62 depends on the temporomandibular joint positions and movements being determined or measured by the upper face reference device 50 and the method according to the present invention, as will be understood by those with skill in the art with respect to this disclosure. In one embodiment, the one or more than one marker 62 of the upper face reference device 50 is two markers. In another embodiment, the one or more than one marker 62 of the upper face reference device 50 is three markers. In another embodiment, the one or more than one marker 62 of the upper face reference device 50 is four markers. In another embodiment, the one or more than one marker 62 of the upper face reference device 50 is more than four markers.

Figure 29:
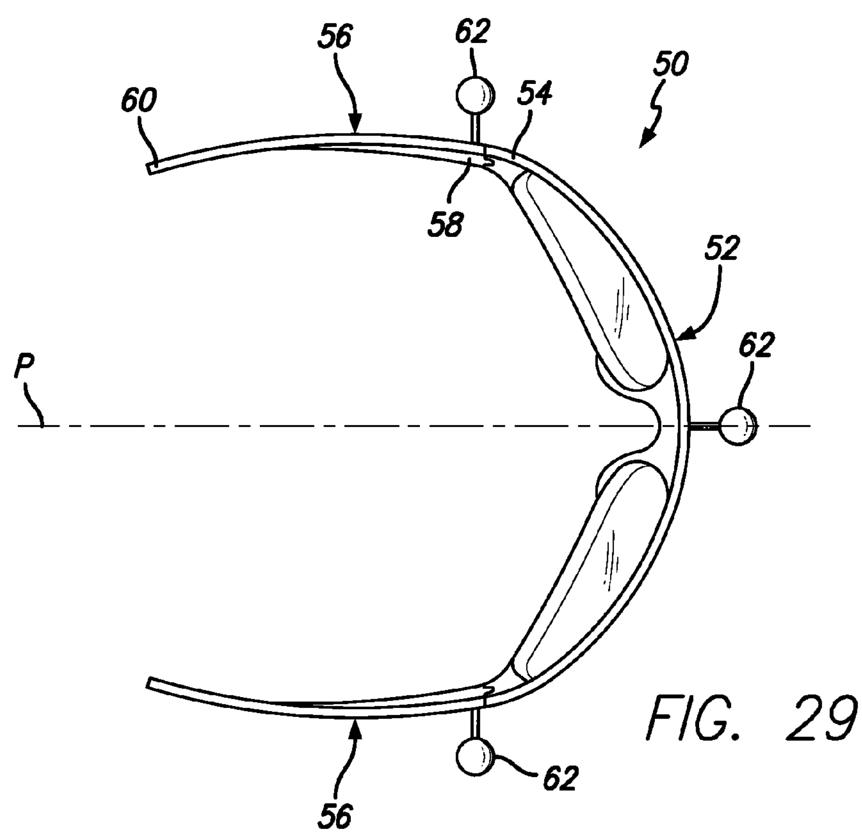
FIG. 29 is a top perspective view of the device shown in FIG. 26.
Figure 30:
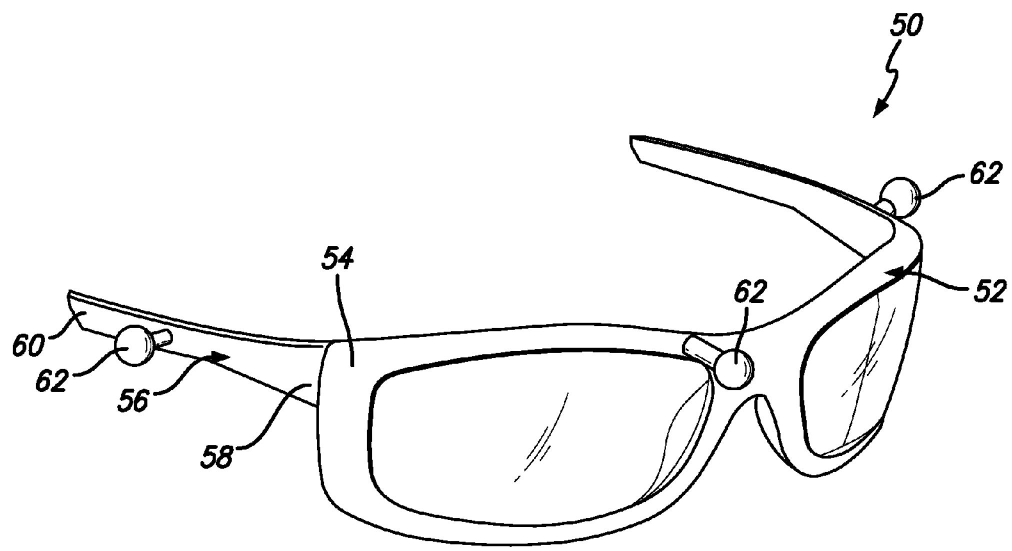
FIG. 30 is a superior, lateral, frontal perspective view of another embodiment of a device for determining or measuring temporomandibular joint positions and movements of a patient according to the present invention.
Figure 31:
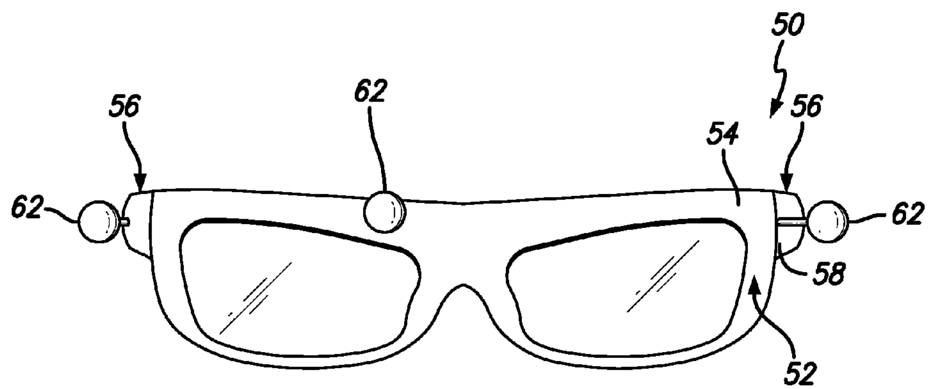
FIG. 31 is a frontal perspective view of the device shown in FIG. 30.
Figure 32:
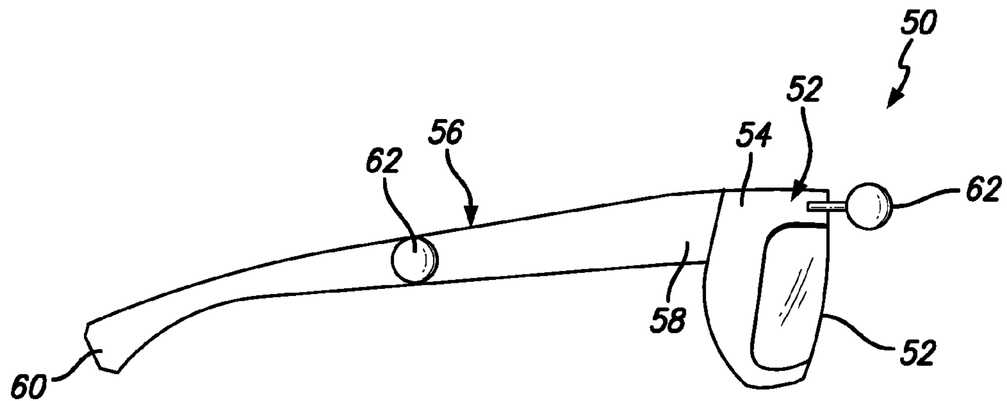
FIG. 32 is a lateral perspective view of the device shown in FIG. 30.

In one embodiment, the upper face reference device 50 is symmetric about the plane 'p,' as shown most clearly in FIG. 29. In another embodiment, the upper face reference device 50 is asymmetric about the plane 'p,' as shown most clearly in FIG. 33. In another embodiment, one of the one or more than one marker 62 is attached to the frontal section 52 coincident with the plane 'p,' as shown most clearly in FIG. 26, FIG. 27 and FIG. 29. In another embodiment, one of the one or more than one marker 62 is attached to the frontal section 52 non-coincident with the plane 'p,' as shown most clearly in FIG. 30, FIG. 31 and FIG. 33. In another embodiment, one of the one or more than one marker 62 is attached to one lateral section 56 a first distance from the anterior end 58 of the lateral section 56, and another of the one or more than one marker 62 is attached to the other lateral section 56 a second distance from the anterior end 58 of the other lateral section 56, and the first distance is equal to the second distance, as shown most clearly in FIG. 26 and FIG. 29. In another embodiment, one of the one or more than one marker 62 is attached to one lateral section 56 a first distance from the anterior end 58 of the lateral section 56, and another of the one or more than one marker 62 is attached to the other lateral section 56 a second distance from the anterior end 58 of the other lateral section 56, and the first distance is unequal to the second distance, as shown most clearly in FIG. 30 and FIG. 33. In another embodiment, one marker 62 is attached to the frontal section 52 coincident with the plane 'p,' another marker 62 is attached to one lateral section 56 a first distance from the anterior end 58 of the lateral section 56, and another marker 62 is attached to the other lateral section 56 a second distance from the anterior end 58 of the other lateral section 56, where the first distance is equal to the second distance, as shown most clearly in FIG. 26 and FIG. 29. In another embodiment, one marker 62 is attached to the frontal section 52 non-coincident with the plane 'p,' another marker 62 is attached to one lateral section 56 a first distance from the anterior end 58 of the lateral section 56, and another marker 62 is attached to the other lateral section 56 a second distance from the anterior end 58 of the other lateral section 56, where the first distance is equal to the second distance, as shown most clearly in FIG. 26 and FIG. 29. In another embodiment, one marker 62 is attached to the frontal section 52 non-coincident with the plane 'p,' another marker 62 is attached to one lateral section 56 a first distance from the anterior end 58 of the lateral section 56, and another marker 62 is attached to the other lateral section 56 a second distance from the anterior end 58 of the other lateral section 56, where the first distance is unequal to the second distance, as shown most clearly in FIG. 26 and FIG. 29.

In one embodiment, all of the one or more than one markers 62 are integrally and non-movably attached to the upper face reference device 50. In another embodiment, one or more of the one or more than one marker 62 is movably attached to the upper face reference device 50. In another embodiment, all of the one or more than one markers 62 are movably attached to the upper face reference device 50. In another embodiment, one or more of the one or more than one marker 62 is removably attached to the upper face reference device 50. In another embodiment, all of the one or more than one markers 62 are removably attached to the upper face reference device 50.

In one embodiment, the upper face reference device 50 is custom made to fit the patient. In another embodiment, the upper face reference device 50 is selected from a group of standardized sizes available as part of a system according to the present invention to fit the patient.

In one embodiment, one or more of the one or more than one marker 62 is an emitter of electromagnetic radiation. In another embodiment, all of the one or more than one markers 62 are emitters of electromagnetic radiation. In one embodiment, one or more of the one or more than one marker 62 is a reflector of electromagnetic radiation. In another embodiment, all of the one or more than one markers 62 are reflectors of electromagnetic radiation. In one embodiment, one or more of the one or more than one marker 62 is an emitter of electromagnetic radiation, and one or more of the one or more than one marker 62 is a reflector of electromagnetic radiation. The one or more than one marker 62 can emit or reflect electromagnetic radiation in any suitable wavelength, range of wavelengths, group of wavelengths or group of ranges of wavelengths, as will be understood by those with skill in the art with respect to this disclosure. In one embodiment, one or more of the one or more than one marker 62 emits or reflects electromagnetic radiation in the infrared wavelengths. In another embodiment, one or more of the one or more than one marker 62 emits or reflects electromagnetic radiation in the ultraviolet wavelengths. In a preferred embodiment, one or more of the one or more than one marker 62 emits or reflects electromagnetic radiation in the visible wavelengths. In one embodiment, one or more of the one or more than one marker 62 emits or reflects electromagnetic radiation in a first wavelength, range of wavelengths, group of wavelengths or group of ranges of wavelengths, and another of the one or more than one marker 62 emits or reflects electromagnetic radiation in a second wavelength, range of wavelengths, group of wavelengths or group of ranges of wavelengths, where the first wavelength, range of wavelengths, group of wavelengths or group of ranges of wavelengths is different from the second wavelength, range of wavelengths, group of wavelengths or group of ranges of wavelengths which advantageously allows distinction between the markers 62 based on the wavelength, range of wavelengths, group of wavelengths or group of ranges of wavelengths emitted or reflected.

Figure 34:
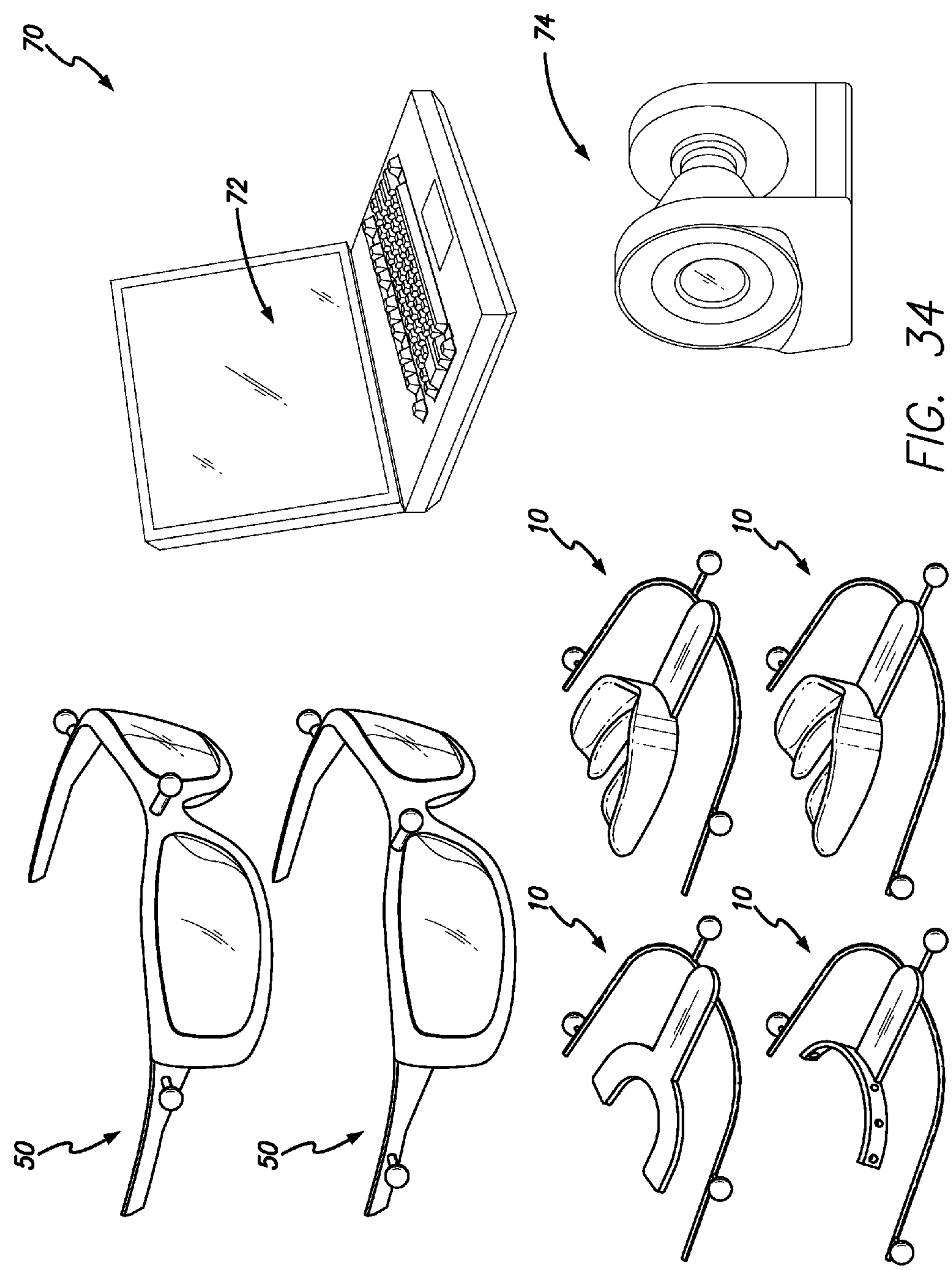
FIG. 34 is a schematic view of a system for measuring temporomandibular joint positions and movements of a patient according to the present invention.

According to one embodiment of the present invention, there is provided a system for determining or measuring temporomandibular joint positions and movements of a patient. The system comprises one or more than one device according to the present invention for determining or measuring temporomandibular joint positions and movements of a patient. Referring now to FIG. 34, there is shown a schematic view of various components of one embodiment of a system according to one embodiment of the present invention. In one embodiment, the system 70 comprises one or more than one mandibular/maxillary reference device 10 according to the present invention for determining or measuring temporomandibular joint positions and movements of a patient or comprises one or more than one upper face reference device 50 according to the present invention for determining or measuring temporomandibular joint positions and movements of a patient. In one embodiment, the system 70 comprises both one or more than one mandibular/maxillary reference device 10 according to the present invention for determining or measuring temporomandibular joint positions and movements of a patient and comprises one or more than one upper face reference device 50 according to the present invention for determining or measuring temporomandibular joint positions and movements of a patient. In one embodiment, the system 70 comprises a plurality of mandibular/maxillary reference devices 10 according to the present invention for determining or measuring temporomandibular joint positions and movements of a patient. In one embodiment, the plurality of mandibular/maxillary reference devices 10 comprise mandibular/maxillary reference devices 10 of at least two different sizes. In one embodiment, the system 70 comprises a plurality of upper face reference devices 50 according to the present invention for determining or measuring temporomandibular joint positions and movements of a patient. In one embodiment, the plurality of upper face reference devices 50 comprise mandibular/maxillary reference devices 10 of at least two different sizes. In one embodiment, the system 70 comprises two mandibular/maxillary reference devices 10 according to the present invention for determining or measuring temporomandibular joint positions and movements of a patient. In one embodiment, the system 70 comprises both two mandibular/maxillary reference devices 10 according to the present invention for determining or measuring temporomandibular joint positions and movements of a patient and comprises one upper face reference device 50 according to the present invention for determining or measuring temporomandibular joint positions and movements of a patient. In one embodiment, the system 70 comprises a plurality of mandibular/maxillary reference devices 10 according to the present invention for determining or measuring temporomandibular joint positions and comprises a plurality of upper face reference devices 50 according to the present invention for determining or measuring temporomandibular joint positions and movements of a patient. In one embodiment, the plurality of mandibular/maxillary reference devices 10 are of at least two different sizes, and the plurality of upper face reference devices 50 are of at least two different sizes.

In one embodiment, the system 70 further comprises a detecting device 72. The detecting device 72 detects electromagnetic radiation reflected off of or emitted from the one or more than one marker 18 attached to the one or more than one mandibular/maxillary reference device 10 or reflected off of or emitted from the one or more than one marker 62 attached to the one or more than one upper face reference device 50, and converts the detected electromagnetic radiation to discrete or real time electronic or printed information.

In one embodiment, the system 70 further comprises an analyzer 74. The analyzer 74 processes the information from the detecting device 72 and determines or measures temporomandibular joint positions and movements of the patient using the information. In one embodiment, the analyzer 74 determines positions of the one or more than one marker 18 on a first mandibular/maxillary reference device 10 applied to a patient with respect to the one or more than one marker 18 on a second mandibular/maxillary reference device 10 applied to the patient, or with respect to one or more than one marker 62 on an upper face reference device 50 applied to the patient, or with respect to both the one or more than one marker 18 on a second mandibular/maxillary reference device 10 applied to the patient and one or more than one marker 62 on an upper face reference device 50 applied to the patient. In another embodiment, the analyzer 74 determines positions of the one or more than one marker 18 on a first mandibular/maxillary reference device 10 applied to a patient with respect to the one or more than one marker 18 on a second mandibular/maxillary reference device 10 applied to the patient, or with respect to one or more than one marker 62 on an upper face reference device 50 applied to the patient, or with respect to both the one or more than one marker 18 on a second mandibular/maxillary reference device 10 applied to the patient and one or more than one marker 62 on an upper face reference device 50 applied to the patient at a plurality of predetermined times, and thereby determines values of one or more than one temporomandibular joint position or movement of the patient. In one embodiment, the plurality of predetermined times is two predetermined times. In another embodiment, the plurality of predetermined times is three predetermined times. In another embodiment, the plurality of predetermined times is four predetermined times. In another embodiment, the plurality of predetermined times is more than four predetermined times. In one embodiment, the analyzer 74 determines the values of the temporomandibular joint positions and movements in real time. In one embodiment, the analyzer 74 is a computer; however, the analyzer 74 can be any suitable device for computation, such as, for example, a field programmable gate array or an embedded processor, as will be understood by those with skill in the art with respect to this disclosure. In one embodiment, the analyzer 74 comprises a display for displaying the positions and values determined. In another embodiment, the analyzer 74 transmits the positions and values to a separate display. In one embodiment, the analyzer 74 stores the positions and values. In one embodiment, the positions and values are determined in two dimensions. In a preferred embodiment, the positions and values are determined in two dimensions at a single time. In a preferred embodiment, the positions and values are determined in two dimensions over a period of time or at multiple times. In a preferred embodiment, the positions and values are determined in three dimensions at a single time. In a preferred embodiment, the positions and values are determined in three dimensions over a period of time or at multiple times. In another preferred embodiment, the positions and values are used to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment. In one embodiment, the detecting device 72 and the analyzer 74 are combined into one unit.

The device and the system of the present invention and their component parts can comprise any suitable material for the intended purpose, as will be understood by those with skill in the art with reference to this disclosure. In one embodiment, the device, the system or their component parts comprise a material selected from the group consisting of a biocompatible polymer, a light weight fiber-reinforced resin, a polymer composite and stainless steel. In one embodiment, the device comprises one or more than one biocompatible material capable of being sterilized.

Figure 35:
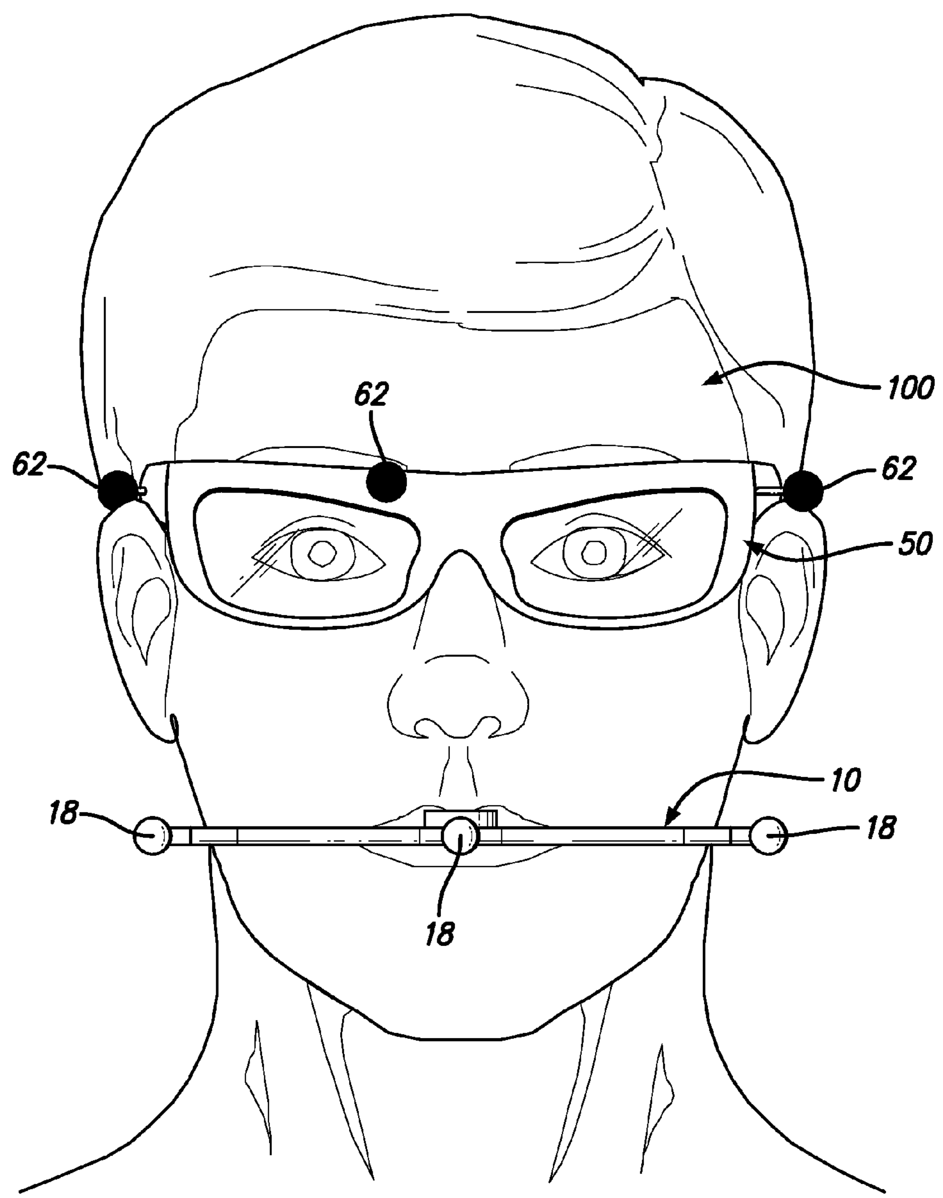
FIG. 35 is a schematic frontal perspective view of the head of a patient with an upper face reference device applied to the upper face of a patient and a mandibular/maxillary reference device according to the present invention applied to the mandible of a patient with the mandible moving from a first position to two other positions (shown in broken lines)
Figure 36:
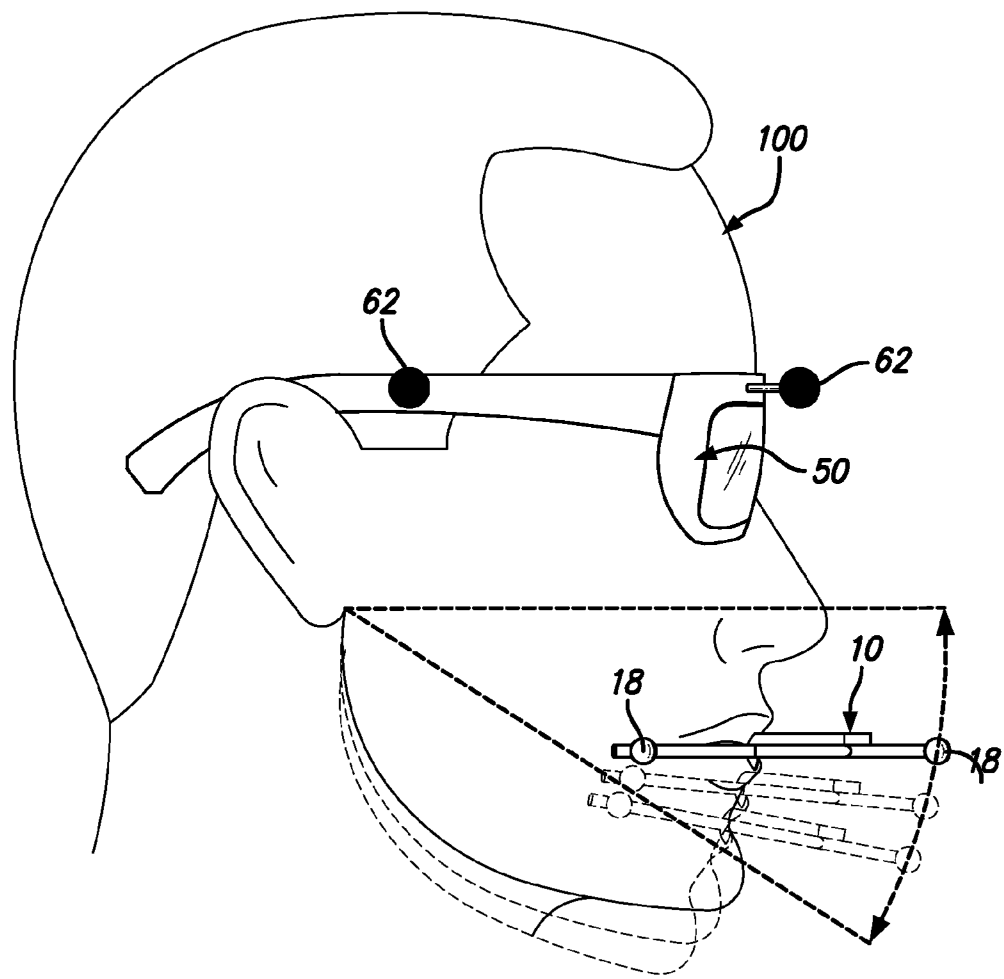
FIG. 36 is a schematic lateral perspective view of the head of the patient as shown in FIG. 35.
Figure 37:
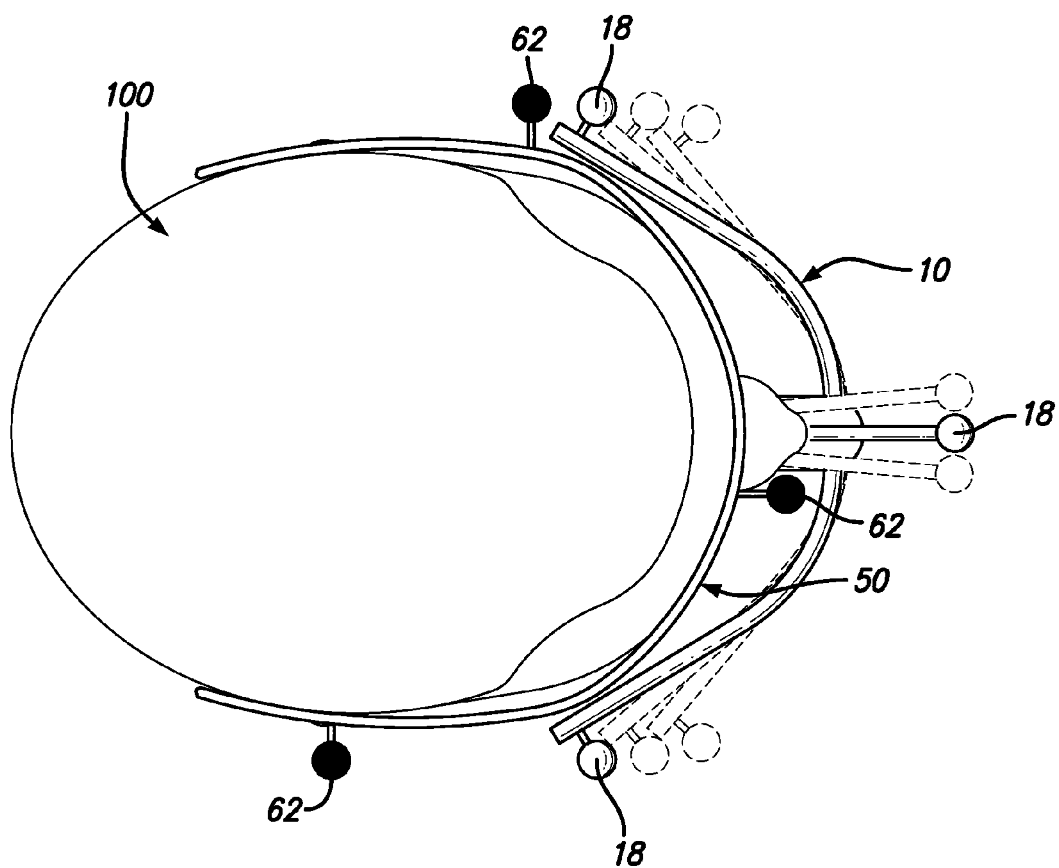
FIG. 37 is a schematic top perspective view of the head of the patient as shown in FIG. 35.

According to another embodiment of the present invention, there is provided a method for determining or measuring one or more than one temporomandibular joint position or movement of a patient having an upper face, a maxilla with maxillary teeth, and a mandible with mandibular teeth. The method comprises providing a device according to the present invention or providing a system according to the present invention and using the device or using the system to determine or measure one or more than one temporomandibular joint position or movement of the patient. Referring now to FIG. 35, FIG. 36 and FIG. 37, there are shown, respectively, a schematic frontal perspective view of the head of a patient with an upper face reference device applied to the upper face of the patient and a mandibular/maxillary reference device according to the present invention applied to the mandible of the patient with the mandible moving from a first position to two other positions (shown in broken lines) (FIG. 35), a schematic lateral perspective view of the head of the patient as shown in FIG. 35 (FIG. 36), and a schematic top perspective view of the head of the patient as shown in FIG. 35 (FIG. 37). As can be seen, in one embodiment, the method comprises providing a mandibular/maxillary reference device 10 according to the present invention, applying the mandibular/maxillary reference device 10 to the mandibular teeth of the patient 100. The method further comprises providing an upper face reference device 50 according to the present invention, and applying the upper face reference device 50 to the upper face of the patient 100. In one embodiment, applying the mandibular/maxillary reference device 10 comprises removably bonding the mandibular/maxillary reference device 10 to the mandibular teeth of the patient 100. Then, electromagnetic radiation is reflected off of one or more than one of the one or more than one marker 18 of the mandibular/maxillary reference device 10 and one or more than one of the one or more than one marker 62 of the upper face reference device 50, or electromagnetic radiation is emitted from one or more than one of the one or more than one marker 18 of the mandibular/maxillary reference device 10 and one or more than one of the one or more than one marker 62 of the upper face reference device 50, or electromagnetic radiation is both reflected off of one or more than one of the one or more than one marker 18 of the mandibular/maxillary reference device 10 and the one or more than one marker 62 of the upper face reference device 50, and electromagnetic radiation is emitted from one or more than one of the one or more than one marker 18 of the mandibular/maxillary reference device 10 and the one or more than one marker 62 of the upper face reference device 50. Next, the method comprises providing a detecting device, and the electromagnetic radiation reflected off of or emitted from the one or more than one marker 18 of the mandibular/maxillary reference device 10 and the one or more than one marker 62 of the upper face reference device 50 is detected by the detecting device, and the detecting device converts the detected electromagnetic radiation to discrete or real time electronic or printed information. In one embodiment, the detecting device further records the information. In another embodiment, the detecting device transmits the information to an analyzer. In one embodiment, the analyzer processes the information transmitted by the detecting device and determines values of one or more than one temporomandibular joint position or movement of the patient. In one embodiment, the analyzer determines the values of one or more than one temporomandibular joint position or movement of the patient at a plurality of predetermined times. In one embodiment, the plurality of plurality of predetermined times is two times. In one embodiment, the plurality of plurality of predetermined times is three times. In one embodiment, the plurality of plurality of predetermined times is four times. In one embodiment, the plurality of plurality of predetermined times is more than four times. In one embodiment, the analyzer determines the values of one or more than one temporomandibular joint position or movement of the patient in real time. In one embodiment, the analyzer determines the values of one or more than one temporomandibular joint position or movement of the patient over a period of time. In one embodiment, the period of time is between 3 seconds and 3 minutes. In one embodiment, the analyzer determines the values of one or more than one temporomandibular joint position or movement of the patient in two dimensions. In one embodiment, the analyzer determines the values of one or more than one temporomandibular joint position or movement of the patient in three dimensions. In one embodiment, the analyzer comprises a display for displaying the information transmitted and the values of one or more than one temporomandibular joint position or movement of the patient, and the method further comprises displaying the information. In another embodiment, the analyzer transmits the values of the values of one or more than one temporomandibular joint position or movement of the patient to a separate display, and the method further comprises displaying the values. In a preferred embodiment, the values are used to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment. Referring again to FIG. 35, FIG. 36 and FIG. 37, as can be seen, when the mandible moves from a first position to a second position and a third position (broken lines), the markers 62 (dark) of the upper face reference device 50 remain stationary in space while the markers 18 on the mandibular/maxillary reference device 10 move in space relative to their first position and relative to the position of the one or more than one marker 62 of the upper face reference device 50. By detecting the position of the one or more than one marker 18 of the mandibular/maxillary reference device 10 relative to the one or more than one marker 62 of the upper face reference device 50, and transmitting the information detected to the analyzer, the analyzer can determine the values of one or more than one temporomandibular joint position or movement of the patient. Further as can be seen, having dissimilar markers 18 on the mandibular/maxillary reference device 10 as compared to the markers 62 on the upper face reference device 50, such as for example, color, disalignment, or dissimilar emission or reflective characteristics, assists in determining the values of one or more than one temporomandibular joint position or movement of the patient.

According to another embodiment of the present invention, there is provided another method for determining or measuring one or more than one temporomandibular joint position or movement of a patient having an upper face, a maxilla with maxillary teeth, and a mandible with mandibular teeth. The method comprises providing a device according to the present invention or providing a system according to the present invention and using the device or using the system to determine or measure one or more than one temporomandibular joint position or movement of the patient. Referring now to FIG. 38, FIG. 39 and FIG. 40, there are shown, respectively, a schematic frontal perspective view of the head of the patient with a first mandibular/maxillary reference device according to the present invention applied to the maxilla of the patient and a second mandibular/maxillary reference device according to the present invention applied to the mandible of the patient with the mandible moving from a first position to two other positions (shown in broken lines) (FIG. 38), a schematic lateral perspective view of the head of the patient as shown in FIG. 38 (FIG. 39), and a schematic top perspective view of the head of the patient as shown in FIG. 38 (FIG. 40). As can be seen, in one embodiment, the method comprises providing a first mandibular/maxillary reference device 10' according to the present invention applying the first mandibular/maxillary reference device 10' to the mandibular teeth of the patient 100. The method further comprises providing a second mandibular/maxillary reference device 10" according to the present invention applying the mandibular/maxillary reference device 10" to the maxillary teeth of the patient 100. In one embodiment, applying the mandibular/maxillary reference 10', 10" comprises removably bonding the mandibular/maxillary reference device 10', 10" to the mandibular teeth or maxillary teeth of the patient 100. Then, electromagnetic radiation is reflected off of one or more than one of the one or more than one marker 18 of the first mandibular/maxillary reference device 10' and one or more than one of the one or more than one marker 18 of the second mandibular/maxillary reference device 10", or electromagnetic radiation is emitted from one or more than one of the one or more than one marker 18 of the first mandibular/maxillary reference device 10' and one or more than one of the one or more than one marker 18 of the second mandibular/maxillary reference device 10", or electromagnetic radiation is both reflected off of one or more than one of the one or more than one marker 18 of the first mandibular/maxillary reference device 10' and the one or more than one marker 18 of the second mandibular/maxillary reference device 10" and electromagnetic radiation is emitted from one or more than one of the one or more than one marker 18 of the first mandibular/maxillary reference device 10' and the one or more than one marker 18 of the second mandibular/maxillary reference device 10". Next, the method comprises providing a detecting device, and the electromagnetic radiation reflected off of or emitted from the one or more than one marker 18 of the first mandibular/maxillary reference device 10' and the one or more than one marker 18 of the second mandibular/maxillary reference device 10" is detected by the detecting device, and the detecting device converts the detected electromagnetic radiation to discrete or real time electronic or printed information. In one embodiment, the detecting device further records the information. In another embodiment, the detecting device transmits the information to an analyzer. In one embodiment, the analyzer processes the information transmitted by the detecting device and determines values of one or more than one temporomandibular joint position or movement of the patient. In one embodiment, the analyzer determines the values of one or more than one temporomandibular joint position or movement of the patient at a plurality of predetermined times. In one embodiment, the plurality of plurality of predetermined times is two times. In one embodiment, the plurality of plurality of predetermined times is three times. In one embodiment, the plurality of plurality of predetermined times is four times. In one embodiment, the plurality of plurality of predetermined times is more than four times. In one embodiment, the analyzer determines the values of one or more than one temporomandibular joint position or movement of the patient in real time. In one embodiment, the analyzer determines the values of one or more than one temporomandibular joint position or movement of the patient over a period of time. In one embodiment, the period of time is between 3 seconds and 3 minutes. In one embodiment, the analyzer determines the values of one or more than one temporomandibular joint position or movement of the patient in two dimensions. In one embodiment, the analyzer determines the values of one or more than one temporomandibular joint position or movement of the patient in three dimensions. In one embodiment, the analyzer comprises a display for displaying the information transmitted and the values of one or more than one temporomandibular joint position or movement of the patient, and the method further comprises displaying the information. In another embodiment, the analyzer transmits the values of the values of one or more than one temporomandibular joint position or movement of the patient to a separate display, and the method further comprises displaying the values. In a preferred embodiment, the values are used to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment. Referring again to FIG. 38, FIG. 39 and FIG. 40, as can be seen, when the mandible moves from a first position to a second position and a third position (broken lines), the markers 18 (dark) on the second mandibular/maxillary reference device 10" remain stationary in space while the marker 18 on the first mandibular/maxillary reference device 10' move in space relative to their first position and relative to the position of the one or more than one marker 18 on the second mandibular/maxillary reference device 10". By detecting the position of the one or more than one marker 18 of the first mandibular/maxillary reference device 10' relative to the one or more than one marker 18 on the second mandibular/maxillary reference device 10", and transmitting the information detected to the analyzer, the analyzer can determine the values of one or more than one temporomandibular joint position or movement of the patient. Further as can be seen, having dissimilar markers 18 on the first mandibular/maxillary reference device 10' as compared to the markers on the second mandibular/maxillary reference device 10", such as for example, color, disalignment, or dissimilar emission or reflective characteristics, assists in determining the values of one or more than one temporomandibular joint position or movement of the patient.

According to another embodiment of the present invention, the upper face of the patient has an auriculo-orbital plane (Frankfurt plane), and the method for determining or measuring one or more than one temporomandibular joint position or movement further comprises determining the variance of the mandibular/maxillary reference device 10' applied to the mandibular teeth of the patient to the auriculo-orbital plane of the patient. Referring now to FIG. 41, FIG. 42, FIG. 43 and FIG. 44, there are shown, respectively, a schematic frontal perspective view of the head of a patient with an upper face reference device according to the present invention applied to the upper face of a patient and a mandibular/maxillary reference device according to the present invention applied to the maxilla of the patient (FIG. 41), and a schematic lateral perspective view of the head of the patient as shown in FIG. 41 (FIG. 42), a schematic frontal perspective view of the head of a patient with a first mandibular/maxillary reference device according to the present invention applied to the maxilla of a patient and a second mandibular/maxillary reference device according to the present invention applied to the mandible of the patient (FIG. 43), and a schematic lateral perspective view of the head of the patient as shown in FIG. 43 (FIG. 44). As can be seen in FIG. 41 and FIG. 42, in one embodiment, determining the variance of the mandibular/maxillary reference device 10' applied to the mandibular teeth of the patient to the auriculo-orbital plane 102 of the patient comprises, first, applying an upper face reference device 50 according to the present invention to the patient, where the position of the markers 62 of the upper face reference device 50 are used to indicate a plane parallel to the auriculo-orbital plane (dashed line) 102, and applying a mandibular/maxillary reference device 10" according to the present invention to the maxillary teeth of the patient. Next, the variance between the auriculo-orbital plane 102 as indicated by the markers 62 on the upper face reference device 50 and mandibular/maxillary reference device 10" applied to the maxillary teeth is determined. Then, the upper face reference device 50 is removed while the mandibular/maxillary reference device 10" is left in place as the second mandibular/maxillary reference device 10". Next, the variance is used in determining or measuring one or more than one temporomandibular joint position or movement of the patient. In another embodiment, as can be seen in FIG. 43 and FIG. 44, determining the variance of the first mandibular/maxillary reference device 10' applied to the mandibular teeth of the patient to the auriculo-orbital plane 102 of the patient 100 comprises, first, applying a mandibular/maxillary reference device 10' to the mandibular teeth, and applying a mandibular/maxillary reference device 10" according to the present invention to the maxillary teeth of the patient 100. In one embodiment, as shown in FIG. 1, FIG. 2, FIG. 3 and FIG. 4, the mandibular/maxillary reference device 10' applied to the mandibular teeth comprises a mouthpiece 12 that is a dental tray. In another embodiment, as shown in FIG. 5, FIG. 6, FIG. 7 and FIG. 8, the mandibular/maxillary reference device 10 applied to the mandibular teeth comprises a mouthpiece 12 that is an occlusal plane indexing plate. Next, the patient occludes the maxillary teeth and mandibular teeth creating an occlusion plane as marked by the markers 18 on the mandibular/maxillary reference device 10' applied to the mandibular teeth, and the variance between the auriculo-orbital plane 102 and the occlusion plane is assumed to be a known deviation, such as for example 8° or 10°, as will be understood by those with skill in the art with respect to this disclosure. Then, the variance between the auriculo-orbital plane 102 and the mandibular/maxillary reference device 10" applied to the maxillary teeth is determined. Next, the mandibular/maxillary reference device 10' is removed from the mandibular teeth while the mandibular/maxillary reference device 10" is left in place as the second mandibular/maxillary reference device 10". Then, the variance between the first mandibular/maxillary reference device 10' and the auriculo-orbital plane 102 is used in determining or measuring one or more than one temporomandibular joint position or movement of the patient.

According to another embodiment of the present invention, there is provided a method of diagnosing a condition or disease of the temporomandibular joint of a patient. The method comprises, first, identifying a patient with a potential temporomandibular joint condition or disease for which measurement of temporomandibular joint positions and movements could aid in the diagnosis or treatment of the temporomandibular joint condition or disease. Next, values for one or more than one temporomandibular joint position or movement are determined or measured according to the present invention. Then, the values for the one or more than one temporomandibular joint position or movement of the patient are used to diagnose the condition or disease of the temporomandibular joint of the patient or the lack of a condition or disease of the temporomandibular joint of the patient.

According to another embodiment of the present invention, there is provided a method of treating a condition or disease of the temporomandibular joint of a patient. The method comprises, first, diagnosing a condition or disease of the temporomandibular joint of a patient according to the present invention. Next, the method comprises treating the patient.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference in their entirety.

What is claimed is:

1. A method for determining or measuring values of one or more than one temporomandibular joint position or movement of a patient having a cranium with eyes, a nose with a bridge, an auricle with a superior aspect, an upper face, a maxilla with maxillary teeth and an inferior anterior portion, and a mandible with mandibular teeth and a superior anterior portion, the method comprising:

a) providing a mandibular/maxillary reference device, the device comprising:
   i) a mouthpiece configured to fit the inferior anterior portion of the maxilla of the patient or the superior anterior portion of the mandible of the patient, the mouthpiece comprising an anterior end and a posterior end, and a plane 'p' passing from the anterior end of the mouthpiece to the posterior end of the mouthpiece;
   ii) one or more than one support comprising a first posterior end, a second posterior end, an axial length 'l' from the first posterior end to the second posterior end, and one or more than one attachment position;
   iii) one or more than one attachment element attaching the one or more than one support to the mouthpiece, where the one or more than one attachment element attaches the support to the mouthpiece at the one or more than one attachment position along the length 'l';
   iv) one or more than one marker attached to the one or more than one support;
   where the mouthpiece is configured to interchangeably and reversibly fit both the inferior anterior portion of the maxilla of the patient and the superior anterior portion of the mandible of the patient by rotating the mandibular/maxillary reference device around an axis passing from the anterior end of the mouthpiece to the posterior end of the mouthpiece in plane 'p' and applying the mandibular/maxillary reference device to the mandibular teeth of the patient;

b) providing an upper face reference device, the device comprising:
   i) a frontal section configured to fit over the eyes and the bridge of the nose of the patient, the frontal section comprising two lateral ends and a length 'l' between the two lateral ends, and a plane 'p' passing equidistantly between one lateral end of the frontal section and the other lateral end of the frontal section;
   ii) two lateral sections, each lateral section configured to fit between the superior aspect of the auricle and the cranium of the patient, where each lateral section comprises an anterior end and a posterior end, where the anterior end of each lateral section is attached to one of the two lateral ends of the frontal section; and
   iii) one or more than one marker attached to the frontal section, or to one or both of the lateral sections, or to both the frontal section and to one or both of the lateral sections;
   and applying the upper face reference device to the upper face of the patient;

c) reflecting electromagnetic radiation off of one or more than one of the one or more than one marker of the mandibular/maxillary reference device and one or more than one of the one or more than one marker of the upper face reference device, or emitting electromagnetic radiation from one or more than one of the one or more than one marker of the mandibular/maxillary reference device and one or more than one of the one or more than one marker of the upper face reference device, or both reflecting electromagnetic radiation off of one or more than one of the one or more than one marker of the mandibular/maxillary reference device and the one or more than one marker of the upper face reference device and emitting electromagnetic radiation from one or more than one of the one or more than one marker of the mandibular/maxillary reference device and the one or more than one marker of the upper face reference device; and d) providing a detecting device, and detecting the electromagnetic radiation reflected off of or emitted from the one or more than one marker of the mandibular/maxillary reference device and the one or more than one marker of the upper face reference device is detected by the detecting device, where the detecting device converts the detected electromagnetic radiation to discrete or real time electronic or printed information.

2. The method of claim 1, where applying the mandibular/maxillary reference device comprises removably bonding the mandibular/maxillary reference device to the mandibular teeth of the patient.

3. The method of claim 1, further comprising recording the information by the detecting device.

4. The method of claim 1, further comprising transmitting the information by the detecting device to an analyzer.

5. The method of claim 4, further comprising processing the information transmitted by the detecting device by the analyzer, and determining the values of one or more than one temporomandibular joint position or movement of the patient by the analyzer.

6. The method of claim 5, further comprising determining the values of one or more than one temporomandibular joint position or movement of the patient at a plurality of predetermined times.

7. The method of claim 6, where the plurality of predetermined times is two times.

8. The method of claim 6, where the plurality of predetermined times is three times.

9. The method of claim 6, where the plurality of predetermined times is four times.

10. The method of claim 6, where the plurality of predetermined times is more than four times.

11. The method of claim 6, where the analyzer determines the values of one or more than one temporomandibular joint position or movement of the patient in real time.

12. The method of claim 6, where the analyzer determines the values of one or more than one temporomandibular joint position or movement of the patient over a period of time.

13. The method of claim 12, where the period of time is between 3 seconds and 3 minutes.

14. The method of claim 6, where the analyzer determines the values of one or more than one temporomandibular joint position or movement of the patient in two dimensions.

15. The method of claim 6, where the analyzer determines the values of one or more than one temporomandibular joint position or movement of the patient in three dimensions.

16. The method of claim 5, where the analyzer comprises a display for displaying the information transmitted and the values of one or more than one temporomandibular joint position or movement of the patient, and the method further comprises displaying the information.

17. The method of claim 5, further comprising transmitting the values of one or more than one temporomandibular joint position or movement of the patient to a separate display by the analyzer, and displaying the values.

18. The method of claim 5, further comprising using the values to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment.

19. The method of claim 1, where the markers on the mandibular/maxillary reference device are dissimilar to the markers on the upper face reference device.

20. The method of claim 19, where the dissimilarity is selected from the group consisting of color, alignment, or emission or reflective characteristics.

21. The method of claim 1, where the mandibular/maxillary reference device applied to the mandibular teeth comprises a mouthpiece is an occlusal plane indexing plate.

22. A method for determining or measuring values of one or more than one temporomandibular joint position or movement of a patient having an upper face, a maxilla with maxillary teeth and an inferior anterior portion, and a mandible with mandibular teeth and a superior anterior portion, the method comprising:

a) providing a first mandibular/maxillary reference device, the first device comprising:

i) a mouthpiece configured to fit the inferior anterior portion of the maxilla of the patient or the superior anterior portion of the mandible of the patient, the mouthpiece comprising an anterior end and a posterior end, and a plane 'p' passing from the anterior end of the mouthpiece to the posterior end of the mouthpiece;

ii) one or more than one support comprising a first posterior end, a second posterior end, an axial length 'l' from the first posterior end to the second posterior end, and one or more than one attachment position;

iii) one or more than one attachment element attaching the one or more than one support to the mouthpiece, where the one or more than one attachment element attaches the support to the mouthpiece at the one or more than one attachment position along the length 'l';

iv) one or more than one marker attached to the one or more than one support;

where the mouthpiece is configured to interchangeably and reversibly fit both the inferior anterior portion of the maxilla of the patient and the superior anterior portion of the mandible of the patient by rotating the mandibular/maxillary reference device around an axis passing from the anterior end of the mouthpiece to the posterior end of the mouthpiece in plane 'p' and applying the first mandibular/maxillary reference device to the mandibular teeth of the patient;

b) providing a second mandibular/maxillary reference device, the second device comprising:

i) a mouthpiece configured to fit the inferior anterior portion of the maxilla of the patient or the superior anterior portion of the mandible of the patient, the mouthpiece comprising an anterior end and a posterior end, and a plane 'p' passing from the anterior end of the mouthpiece to the posterior end of the mouthpiece;

ii) one or more than one support comprising a first posterior end, a second posterior end, an axial length 'l' from the first posterior end to the second posterior end, and one or more than one attachment position;

iii) one or more than one attachment element attaching the one or more than one support to the mouthpiece, where the one or more than one attachment element attaches the support to the mouthpiece at the one or more than one attachment position along the length 'l';

iv) one or more than one marker attached to the one or more than one support;

where the mouthpiece is configured to interchangeably and reversibly fit both the inferior anterior portion of the maxilla of the patient and the superior anterior portion of the mandible of the patient by rotating the mandibular/maxillary reference device around an axis passing from the anterior end of the mouthpiece to the posterior end of the mouthpiece in plane 'p' and applying the second mandibular/maxillary reference device to the mandibular teeth of the patient;

c) reflecting electromagnetic radiation off of one or more than one of the one or more than one marker of the first mandibular/maxillary reference device and one or more than one of the one or more than one marker of the second mandibular/maxillary reference device, or emitting electromagnetic radiation from one or more than one of the one or more than one marker of the first mandibular/maxillary reference device and one or more than one of the one or more than one marker of the second mandibular/maxillary reference device, or both reflecting electromagnetic radiation off of one or more than one of the one or more than one marker of the first mandibular/maxillary reference device and the one or more than one marker of the second mandibular/maxillary reference device and emitting electromagnetic radiation from one or more than one of the one or more than one marker of the first mandibular/maxillary reference device and the one or more than one marker of the second mandibular/maxillary reference device; and d) providing a detecting device, and detecting the electromagnetic radiation reflected off of or emitted from the one or more than one marker of the first mandibular/maxillary reference device and the one or more than one marker of the second mandibular/maxillary reference device is detected by the detecting device, where the detecting device converts the detected electromagnetic radiation to discrete or real time electronic or printed information.

23. The method of claim 22, where applying the first mandibular/maxillary reference device or applying the second mandibular/maxillary reference device comprises removably bonding the first mandibular/maxillary reference device to the mandibular teeth of the patient or removably bonding the second mandibular/maxillary reference device to the maxillary teeth of the patient.

24. The method of claim 22, further comprising recording the information by the detecting device.

25. The method of claim 22, further comprising transmitting the information by the detecting device to an analyzer.

26. The method of claim 25, further comprising processing the information transmitted by the detecting device by the analyzer, and determining the values of one or more than one temporomandibular joint position or movement of the patient by the analyzer.

27. The method of claim 26, further comprising determining the values of one or more than one temporomandibular joint position or movement of the patient at a plurality of predetermined times.

28. The method of claim 27, where the plurality of predetermined times is two times.

29. The method of claim 27, where the plurality of predetermined times is three times.

30. The method of claim 27, where the plurality of predetermined times is four times.

31. The method of claim 27, where the plurality of predetermined times is more than four times.

32. The method of claim 27, where the analyzer determines the values of one or more than one temporomandibular joint position or movement of the patient in real time.

33. The method of claim 27, where the analyzer determines the values of one or more than one temporomandibular joint position or movement of the patient over a period of time.

34. The method of claim 33, where the period of time is between 3 seconds and 3 minutes.

35. The method of claim 27, where the analyzer determines the values of one or more than one temporomandibular joint position or movement of the patient in two dimensions.

36. The method of claim 27, where the analyzer determines the values of one or more than one temporomandibular joint position or movement of the patient in three dimensions.

37. The method of claim 26, where the analyzer comprises a display for displaying the information transmitted and the values of one or more than one temporomandibular joint position or movement of the patient, and the method further comprises displaying the information.

38. The method of claim 26, further comprising transmitting the values of one or more than one temporomandibular joint position or movement of the patient to a separate display by the analyzer, and displaying the values.

39. The method of claim 26, further comprising using the values to calculate a parameter selected from the group consisting of anterior guidance, Bennett angle, condylar guidance, condylar inclination, condylar settings, immediate mandibular translation analogue, immediate side shift, mediotrusion/laterotrusion, orbiting path adjustment, progressive side shift, radial shift, rear wall, retrusion/protrusion, surtrusion/detrusion, top wall and vertical axis adjustment.

40. The method of claim 22, where the markers on the first mandibular/maxillary reference device are dissimilar to the markers on the second mandibular/maxillary reference device.

41. The method of claim 40, where the dissimilarity is selected from the group consisting of color, alignment, or emission or reflective characteristics.

42. The method of claim 22, where the upper face of the patient has an auriculo-orbital plane (Frankfurt plane), and where the method further comprises determining the variance of the first mandibular/maxillary reference device applied to the mandibular teeth of the patient from the auriculo-orbital plane of the patient.

43. The method of claim 42, where determining the variance of the first mandibular/maxillary reference device applied to the mandibular teeth of the patient from the auriculo-orbital plane of the patient comprises:

a) applying an upper face reference device comprising markers to the patient, where the positions of the markers on the upper face reference device are used to indicate the auriculo-orbital plane, and applying a mandibular/maxillary reference device to the maxillary teeth of the patient;

b) determining the variance between the auriculo-orbital plane as indicated by the position of the markers on the upper face reference device and mandibular/maxillary reference device applied to the maxillary teeth;

c) removing the upper face reference device; and d) using the variance in determining or measuring one or more than one temporomandibular joint position or movement of the patient.

44. The method of claim 43, where determining the variance of the first mandibular/maxillary reference device applied to the mandibular teeth of the patient from the auriculo-orbital plane of the patient comprises:

a) applying a mandibular/maxillary reference device comprising markers to the mandibular teeth;

b) applying a mandibular/maxillary reference device to the maxillary teeth of the patient;

c) having the patient occlude the maxillary teeth and mandibular teeth creating an occlusion plane as represented by the markers on the mandibular/maxillary reference device on the mandibular teeth;

d) assuming the variance between the auriculo-orbital plane and the occlusion plane is a known deviation;

e) determining the variance between the auriculo-orbital plane and mandibular/maxillary reference device applied to the maxillary teeth using the assumed variance;

f) removing the mandibular/maxillary reference device from the mandibular teeth while leaving the mandibular/maxillary reference device applied to the maxillary teeth as the second mandibular/maxillary reference device for the method of determining or measuring one or more than one temporomandibular joint position or movement of a patient; and g) using the variance between the auriculo-orbital plane and mandibular/maxillary reference device applied to the maxillary teeth in determining or measuring one or more than one temporomandibular joint position or movement of the patient.

45. The method of claim 44, where the known deviation between the auriculo-orbital plane and the occlusion plane is between 8° and 10°.

46. A method of diagnosing a condition or disease of the temporomandibular joint of a patient, the method comprising:

a) identifying a patient with a potential temporomandibular joint condition or disease;

b) determining or measuring values for one or more than one temporomandibular joint position or movement of the patient according to claim 1; and c) using the values for the one or more than one temporomandibular joint position or movement of the patient to diagnose the condition or disease of the temporomandibular joint of the patient or the lack of a condition or disease of the temporomandibular joint of the patient.

47. A method of diagnosing a condition or disease of the temporomandibular joint of a patient, the method comprising:

a) identifying a patient with a potential temporomandibular joint condition or disease;

b) determining or measuring values for one or more than one temporomandibular joint position or movement of the patient according to claim 22; and c) using the values for the one or more than one temporomandibular joint position or movement of the patient to diagnose the condition or disease of the temporomandibular joint of the patient or the lack of a condition or disease of the temporomandibular joint of the patient.

48. A method of treating a condition or disease of the temporomandibular joint of a patient, the method comprising:

a) diagnosing a condition or disease of the temporomandibular joint of a patient according to claim 46; and b) treating the patient.

49. A method of treating a condition or disease of the temporomandibular joint of a patient, the method comprising:

a) diagnosing a condition or disease of the temporomandibular joint of a patient according to claim 47; and b) treating the patient.

* * * * *